(12) United States Patent
Greaves et al.

(10) Patent No.: US 8,398,722 B2
(45) Date of Patent: Mar. 19, 2013

(54) PHENYLPYRIDO [1,2-A] INDOLIUM-DERIVED THIOL/DISULFIDE DYE, DYE COMPOSITION COMPRISING THIS DYE, PROCESS FOR LIGHTENING KERATIN MATERIALS USING THIS DYE

(75) Inventors: Andrew Greaves, Magny le Hongre (FR); Nicolas Daubresse, La Celles St Cloud (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/679,246

(22) PCT Filed: Sep. 18, 2008

(86) PCT No.: PCT/EP2008/062478
§ 371 (c)(1),
(2), (4) Date: Jul. 12, 2012

(87) PCT Pub. No.: WO2009/037324
PCT Pub. Date: Mar. 26, 2009

(65) Prior Publication Data
US 2012/0266392 A1    Oct. 25, 2012

Related U.S. Application Data

(60) Provisional application No. 60/960,631, filed on Oct. 9, 2007.

(30) Foreign Application Priority Data

Sep. 21, 2007    (FR) ...................................... 07 57781

(51) Int. Cl.
*A61Q 5/10* (2006.01)
(52) U.S. Cl. .............. 8/405; 8/648; 8/587; 8/655; 8/670
(58) Field of Classification Search .............. 8/405, 648, 8/587, 655, 670
See application file for complete search history.

(56) References Cited

U.S. PATENT DOCUMENTS

| | | | |
|---|---|---|---|
| 2,864,813 A | 12/1958 | Bossard et al. | |
| 2,904,385 A | 9/1959 | Charle et al. | |
| 5,034,014 A | 7/1991 | Wenke | |
| 7,247,713 B2 | 7/2007 | David et al. | |
| 7,488,354 B2 | 2/2009 | Daubress et al. | |
| 2007/0130702 A1 | 6/2007 | Andrean et al. | |

FOREIGN PATENT DOCUMENTS

| | | |
|---|---|---|
| DE | 1 544 506 | 4/1970 |
| DE | 198 42 071 | 3/2000 |
| DE | 101 48 844 | 10/2003 |
| EP | 1 133 975 B1 | 9/2001 |
| EP | 1 407 756 | 4/2004 |
| EP | 1 647 580 | 4/2006 |
| EP | 1 672 033 | 6/2006 |
| EP | 1133975 B1 * | 2/2008 |
| FR | 2 787 708 | 6/2000 |
| GB | 1 094 309 | 12/1967 |
| GB | 2 183 237 | 6/1987 |
| JP | 54-8626 | 1/1979 |
| WO | WO 2005/097051 | 10/2005 |
| WO | WO 2006/131163 | 12/2006 |
| WO | WO 2006/134043 | 12/2006 |

OTHER PUBLICATIONS

STIC Search Report dated Sep. 5, 2012.*
Copending U.S. Appl. No. 12/677,450, filed Mar. 10, 2010.
Copending U.S. Appl. No. 12/679,665, filed Mar. 23, 2010.
International Search Report for PCT/EP2008/061885, dated Oct. 22, 2009.
International Search Report for PCT/EP2008/062710, dated Dec. 12, 2008.
English language Abstract of DE 198 42 071, dated Mar. 16, 2000.
English language Derwent Abstract of DE 101 48 844, dated Apr. 10, 2003.
Imahori, H. et al., "Photoinduced Electron Transfer at a Gold Electrode Modified with a Self-Assembled Monolayer of Fullerene," Chem. Commun. vol. 6, pp. 557-558 (1999).
Klepp, J. et al., "Nature of Coenzyme Binding by Glyceraldehyde-3-phophate Dehydrogenase: C NMR Studies with Oxidized [4-13C]Nicotinamide Adenine Dinucleotide," J. Am. Chem. Soc., vol. 111, No. 12, pp. 4440-4447 (1989).
Kniess, T. et al., "Nicotinamide-Substituted Complexes as Redox Markers," J. Labelled. CPD. Radiopharm., vol. XLI, pp. 605-614 (1998).
International Search Report for PCT/EP2008/062478, dated Dec. 3, 2009.
English language abstract of JP 54-8626, Dec. 23, 1979.

* cited by examiner

*Primary Examiner* — Eisa Elhilo
(74) *Attorney, Agent, or Firm* — O'Brien Jones, PLLC.

(57) ABSTRACT

The invention relates to the dyeing of keratin materials using phenylpyrido[1,2-a]indolinium-derived thiol and disulfide fluorescent dyes. The invention relates to a dye composition comprising a phenylpyrido[1,2-a]indolinium-derived-chromophore thiol or disulfide dye and to a dyeing process with a lightening effect on keratin materials, in particular keratin fibers, especially human keratin fibers, such as the hair, using said composition. It similarly relates to novel phenylpyrido [1,2-a]indolinium-derived-chromophore thiol dyes and to the uses thereof in lightening keratin materials. This composition makes it possible to obtain a coloring with a lightening effect which is particularly resistant and visible on dark keratin fibers.

14 Claims, 1 Drawing Sheet

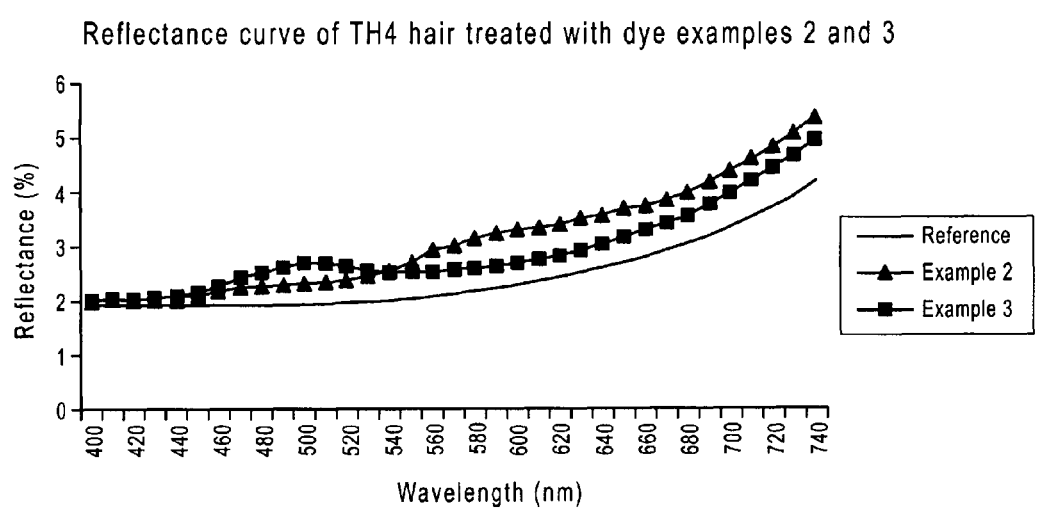

PHENYLPYRIDO [1,2-A] INDOLIUM-DERIVED THIOL/DISULFIDE DYE, DYE COMPOSITION COMPRISING THIS DYE, PROCESS FOR LIGHTENING KERATIN MATERIALS USING THIS DYE

CROSS REFERENCE TO RELATED APPLICATIONS

This application is a national phase application based on PCT/EP2008/062478, filed Sep. 18, 2008, which claims the priority of French Patent Application No. 0757781, filed Sep. 21, 2007; and claims the benefit of U.S. Provisional Application No. 60/960,631, filed Oct. 9, 2007; the content of all of which is incorporated herein by reference.

FIELD OF THE DISCLOSURE

The invention relates to the dyeing of keratin materials using phenylpyrido[1,2-a]indolinium-derived thiol and disulfide fluorescent dyes.

BACKGROUND

It is known practice to dye keratin fibers, in particular human keratin fibers, by direct dyeing. The process conventionally used in direct dyeing comprises applying to the keratin fibers direct dyes which are colored or coloring molecules having an affinity for the fibers, allowing them to diffuse and then rinsing the fibers.

The direct dyes which are conventionally used are, for example, dyes of the nitrobenzene type, anthraquinone dyes, nitropyridine dyes, or dyes of the azo, xanthene, acridine, azine or triarylmethane type. These dyes can also be mixed so as to obtain varied colors. For example, it is known practice to use phenylpyrido[1,2-a]indolinium-derived dyes combined with red or blue direct dyes so as to obtain shiny dark or even black hair (EP 1 133 975).

The lightening of the color of dark keratin fibers to lighter shades, by optionally modifying the shade thereof, constitutes an important demand.

Conventionally, in order to obtain a lighter coloring, a chemical bleaching process is used. This process comprises treating the keratin fibers, such as the hair, with a strong oxidizing system, generally composed of hydrogen peroxide, possibly in combination with persalts, generally in an alkaline medium.

This bleaching system has the drawback of damaging the keratin fibers and of detrimentally affecting their cosmetic properties. The fibers in fact have a tendency to become rough, more difficult to disentangle and more brittle. Finally, the lightening or the bleaching of keratin fibers with oxidizing agents is incompatible with the treatments for modifying the shape of said fibers, particularly in hair straightening treatments.

Another lightening technique comprises applying fluorescent direct dyes to dark hair. This technique, described in particular in documents WO 03/028685 and WO 2004/091473, makes it possible to retain the quality of the keratin fiber during the treatment. However, these fluorescent direct dyes do not exhibit satisfactory fastness with respect to outside agents.

In order to increase the fastness of direct colorings, it is known practice to use disulfide dyes, in particular azo-imidazolium chromophore dyes in patent applications WO 2005/097051 or EP 1647580, and pyridinium/indolinium styryl chromophore dyes in patent applications WO 2006/134043 and WO 2006/136617. None of those documents mentions the problem of lightening keratin fibers without the use of chemical oxidation agents.

SUMMARY

The aim of the present invention is to provide new systems for dyeing keratin materials, in particular human keratin fibers, especially the hair, which do not have the drawbacks of the existing bleaching processes.

In particular, one aim of the invention is to provide dyeing systems for obtaining lightening effects, especially on naturally or artificially dark keratin fibers, which are resistant to successive shampooing operations, which do not damage the keratin fibers and which do not detrimentally affect their cosmetic properties.

Another aim of the invention is to dye keratin materials chromatically, unselectively and homogeneously and in a manner which is persistent with respect to outside attacks, with dyes which are stable in dye compositions.

This aim is achieved with the present invention, a subject of which is a process for dyeing keratin materials, in particular keratin fibers, especially human keratin fibers such as the hair, more particularly dark hair, comprising applying, to the keratin materials, a dye composition comprising, in a suitable cosmetic medium, at least one phenylpyrido[1,2-a]indolinium-derived disulfide or thiol fluorescent dye, chosen from the dyes of formula (I) below:

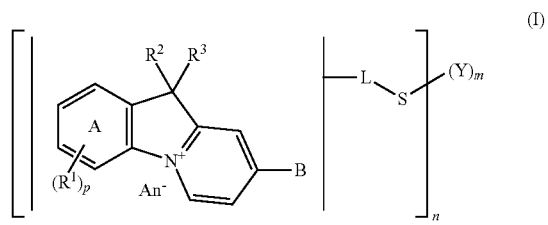

the organic or mineral acid salts, optical isomers and geometric isomers thereof, and the solvates such as hydrates:
in which formula (I):
   m represents 0 or 1;
   n represents 1 or 2;
   p represents an integer between 0 and 4 inclusive, in particular p is 0 or 1;
   $R^1$ represents a halogen atom, an optionally substituted $(C_1\text{-}C_6)$alkyl group, or a $(C_1\text{-}C_6)$alkoxy, $(C_1\text{-}C_6)$alkylthio, $(di)(C_1\text{-}C_6)$-(alkyl)amino, $(C_1\text{-}C_6)$polyhaloalkyl, hydroxyl, $(C_1\text{-}C_6)$polyhydroxyalkyl, polyhydroxy$(C_1\text{-}C_6)$-alkoxy, cyano, R-G-C(G')-, R—C(G')-G-, R'S(O)$_2$—N(R)— or RR'N—S(O)$_2$— group with G or G', which may be identical or different, representing an oxygen or sulfur atom or a group NR', and R and R', which may be identical or different, representing a hydrogen atom or a $(C_1\text{-}C_6)$alkyl group;
   $R^2$ and $R^3$, which may be identical or different, represent a $(C_1\text{-}C_6)$alkyl group, in particular $R^2$ and $R^3$ represent a $(C_1\text{-}C_6)$alkyl group such as methyl;
   B represents an optionally substituted aryl or optionally substituted heteroaryl group, such as optionally substituted phenyl, naphthyl or indolyl;
   L represents a divalent $C_1\text{-}C_{20}$ hydrocarbon-based chain which is optionally substituted, optionally interrupted and/or optionally terminated at one or the other of its ends i) with one or more divalent groups or combinations thereof chosen from: —N(R$_a$)—; —N$^+$(R$_a$)(R$_b$)—, An$^-$; —O—; —S—; —CO— and —SO$_2$— with R$_a$ and R$_b$, which may be identical or different, chosen from a hydrogen, and a (C$_1$-C$_6$)alkyl, hydroxy(C$_1$-C$_6$) alkyl or (di)(C$_1$-C$_6$) (alkyl)amino(C$_1$-C$_6$)alkyl radical, and An$^-$ representing an anionic counterion, or ii) with a cationic heterocycle or cationic heteroaryl Het$^+$, An$^-$, with An$^-$ as defined above and Het$^+$ representing a saturated or unsaturated heterocycle comprising from 5 to 10 members or a heteroaryl comprising from 5 to 10 members, such as imidazolium, piperazinium, piperidinium or benzoimidazolium; in particular, L represents a (C$_1$-C$_6$)alkylene chain linked to the rest of the molecule via a link NR, —NRC(O)— or —C(O)NR—;

Y represents: i) a hydrogen atom; ii) an alkali metal; iii) an alkaline earth metal; iv) an ammonium group: NR$^+$R$^\alpha$R$^\beta$R$^\gamma$R$^\delta$, An$''^-$ or a phosphonium group: P$^+$P$^\alpha$P$^\beta$P$^\gamma$P$^\delta$, An$''^-$ with R$^\alpha$, R$^\beta$, R$^\gamma$ and R$^\delta$, which may be identical or different, representing a hydrogen atom or a (C$_1$-C$_4$)alkyl group, and An$''^-$ an anionic counterion; or v) a thiol-function-protecting group;

An$^-$ represents an anionic counterion;

it being understood that:

when n is 2, then m is zero, and when n is 1, then m is 1, when p is between 2 and 4, the groups R$^1$ are identical or different, the chain -L-S—(Y)$_m$ is linked to the phenylpyrido[1,2-a]indolinium-derived chromophore particularly by A or B.

Another subject of the invention is a dye composition for dyeing keratin fibers with a lightening effect, comprising, in a cosmetic medium, at least one phenylpyrido[1,2-a]indolinium-derived disulfide, thiol or protected thiol fluorescent dye of formula (I) as defined above, and optionally a reducing agent.

A subject of the invention is also novel phenylpyrido[1,2-a]indolinium-derived disulfide or thiol fluorescent dyes of formula (I) as defined above.

The dyeing process according to the invention makes it possible to visibly color dark keratin materials, in particular dark human keratin fibers, especially dark hair. Furthermore, the process of the invention makes it possible to obtain a coloring of the hair, without damaging it, which is persistent with respect to shampooing operations, common attacks (sunlight, perspiration) and hair treatments. The process of the invention also makes it possible to obtain lightening of keratin materials such as keratin fibers, in particular dark keratin fibers, and more particularly dark hair.

Moreover, these dyes extend the color range to yellows and oranges. This process also makes it possible to dye bleached keratin fibers in a strong and chromatic manner.

BRIEF DESCRIPTION OF THE DRAWING

FIG. 1 is a graphical illustration of the reflectance curve of hair treated with compositions according to the disclosure.

DESCRIPTION OF EXEMPLARY EMBODIMENTS

For the purpose of the present invention, the term "dark keratin material" is intended to mean that which exhibits a lightness L* measured in the C.I.E. L*a*b* system of less than or equal to 45, and preferably less than or equal to 40, given that, moreover, L*=0 is equivalent to black and L*=100 is equivalent to white.

For the purpose of the invention, the expression "naturally or artificially dark hair" is intended to mean whose tone height is less than or equal to 6 (dark blond) and preferably less than or equal to 4 (chestnut-brown).

The lightening of the hair is evaluated by the variation in "tone height" before and after application of the compound of formula (I). The notion of "tone" is based on the classification of the natural shades, one tone separating each shade from the shade immediately following or preceding it. This definition and the classification of the natural shades are well known to hair styling professionals and are published in the book "Science des traitements capillaires" [Hair Treatment Sciences], by Charles Zviak 1988, published by Masson, pp. 215 and 278.

The tone heights range from 1 (black) to 10 (very light blond), one unit corresponding to one tone; the higher the figure, the lighter the shade.

An artificially colored hair is a hair whose color has been modified by a dyeing treatment, for example dyeing with direct dyes or oxidation dyes.

For the purpose of the invention, the term "bleached hair" is intended to mean hair whose tone height is greater than 6 and preferably greater than 7.

One means for measuring the lightening effect given to the hair after application of the fluorescent dyes of the invention is to use the phenomenon of hair reflectance.

Preferably, the composition should, after application to dark hair, lead to the results below.

Interest is focused on the hair reflectance performance levels when said hair is irradiated with visible light in the wavelength range from 400 to 700 nanometers.

The curves of reflectance as a function of wavelength, of the hair treated with the composition of the invention and of untreated hair, are then compared.

The curve corresponding to the treated hair should show a reflectance in the wavelength range of from 500 to 700 nanometers which is higher than the curve corresponding to the untreated hair.

This means that, in the wavelength range of from 540 to 700 nanometers, there is at least one range where the reflectance curve corresponding to the treated hair is higher than the reflectance curve corresponding to the untreated hair. The term "higher" is intended to mean a difference of at least 0.05% in reflectance, and preferably of at least 0.1%. All the same, there may be, in the wavelength range of from 540 to 700 nanometers, at least one range where the reflectance curve corresponding to the treated hair is superimposable on or lower than the reflectance curve corresponding to the untreated hair.

Preferably, the wavelength where the difference is at a maximum between the reflectance curve of the treated hair and that of the untreated hair is within the wavelength range of from 500 to 650 nanometers, and preferably within the wavelength range of from 550 to 620 nanometers.

For the purpose of the present invention, and unless otherwise indicated:

the "aryl" or "heteroaryl" radicals or the aryl or heteroaryl part of a radical may be substituted with at least one substituent chosen from:

a C$_1$-C$_{16}$, preferably C$_1$-C$_8$, alkyl radical optionally substituted with one or more radicals chosen from the radicals: hydroxyl, C$_1$-C$_2$ alkoxy, C$_2$-C$_4$(poly)hydroxyalkoxy, acylamino and amino substituted with two C$_1$-C$_4$ alkyl radicals, which may be identical or different, optionally bearing at least one hydroxyl group, or the two radicals possibly forming, with the nitrogen atom to which they are attached, a heterocycle comprising from 5 to 7 members, preferably 5 or 6 members, which is saturated or unsaturated, which is optionally substituted, and which optionally comprises another heteroatom which may be identical or different from the nitrogen;

a halogen atom such as chlorine, fluorine or bromine;

a hydroxyl group;

a $C_1$-$C_2$ alkoxy radical;

$C_1$-$C_2$ alkylthio radical;

a $C_2$-$C_4$ (poly)hydroxyalkoxy radical;

an amino radical;

a 5- or 6-membered heterocycloalkyl radical;

an optionally cationic 5- or 6-membered heteroaryl radical, preferably imidazolium, optionally substituted with a $C_1$-$C_4$ alkyl radical, preferably methyl;

an amino radical substituted with one or two $C_1$-$C_6$ alkyl radicals, which may be identical or different, optionally bearing at least:
  i) one hydroxyl group,
  ii) one amino group optionally substituted with one or two optionally substituted $C_1$-$C_3$ alkyl radicals, said alkyl radicals possibly forming, with the nitrogen atom to which they are attached, a heterocycle comprising from 5 to 7 members, which is saturated or unsaturated, which is optionally substituted, and which optionally comprises at least one other heteroatom which may or may not be different from nitrogen, —N(R)—C(O)R' in which the R radical is a hydrogen atom or a $C_1$-$C_4$ alkyl radical optionally bearing at least one hydroxyl group, and the R' radical is a $C_1$-$C_2$ alkyl radical;

$(R)_2N$—C(O)— in which the R radicals, which may or may not be identical, represent a hydrogen atom, or a $C_1$-$C_4$ alkyl radical optionally bearing at least one hydroxyl group;

R'S(O)$_2$—N(R)— in which the R radical represents a hydrogen atom or a $C_1$-$C_4$ alkyl radical optionally bearing at least one hydroxyl group, and the R' radical represents a $C_1$-$C_4$ alkyl radical or a phenyl radical;

$(R)_2N$—S(O)$_2$— in which the R radicals, which may or may not be identical, represent a hydrogen atom or a $C_1$-$C_4$ alkyl radical optionally bearing at least one hydroxyl group, a carboxylic radical in acid or salified form (preferably with an alkali metal or an ammonium, which is substituted or unsubstituted);

a cyano group;

a polyhaloalkyl group containing from 1 to 6 carbon atoms and from 1 to 6 halogen atoms, which may be identical or different; the polyhaloalkyl group is, for example, trifluoromethyl;

the cyclic or heterocyclic part of a nonaromatic radical may be substituted with at least one substituent, chosen from the groups:

hydroxyl;

$C_1$-$C_4$ alkoxy;

$C_2$-$C_4$ (poly)hydroxyalkoxy;

a $C_1$-$C_2$ alkylthio radical;

RC(O)—N(R')— in which the R' radical is a hydrogen atom or a $C_1$-$C_4$ alkyl radical optionally bearing at least one hydroxyl group, and the R radical is a $C_1$-$C_2$ alkyl radical or an amino radical substituted with two $C_1$-$C_4$ alkyl groups, which may be identical or different, optionally bearing at least one hydroxyl group;

RC(O)—O— in which the R radical is a $C_1$-$C_4$ alkyl radical or an amino radical substituted with one or two $C_1$-$C_4$ alkyl groups, which may be identical or different, optionally bearing at least one hydroxyl group, said alkyl radicals possibly forming, with the nitrogen atom to which they are attached, a heterocycle comprising from 5 to 7 members, which is saturated or unsaturated, which is optionally substituted, and which optionally comprises at least one other heteroatom which may or may not be different from nitrogen;

RO—C(O)— in which the R radical is a $C_1$-$C_4$ alkyl radical optionally bearing at least one hydroxyl group;

a cyclic or heterocyclic radical or a nonaromatic part of an aryl or heteroaryl radical may also be substituted with one or more oxo or thioxo groups;

an "aryl" radical represents a condensed or noncondensed, monocyclic or polycyclic carbon-based group containing from 6 to 22 carbon atoms, and at least one ring of which is aromatic; preferably, the aryl radical is a phenyl, biphenyl, naphthyl, indenyl, anthracenyl or tetrahydronaphthyl;

a "diarylalkyl" radical represents a group comprising, on the same carbon atom of an alkyl group, two aryl groups, which may be identical or different, such as diphenylmethyl or 1,1-diphenylethyl;

a "heteroaryl radical" represents an optionally cationic, condensed or noncondensed, monocyclic or polycyclic group comprising from 5 to 22 members and from 1 to 6 heteroatoms chosen from a nitrogen, oxygen, sulfur and selenium atom, and at least one ring of which is aromatic; preferably, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenooxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, triazolyl, thiazolopyridinyl, thiazoylimidazolyl, thiopyrylyl, triazolyl, xanthylyl and its ammonium salt;

a "diheteroarylalkyl" radical represents a group comprising, on the same carbon atom of an alkyl group, two heteroaryl groups, which may be identical or different, such as difurylmethyl, 1,1-difurylethyl, dipyrrolylmethyl or dithienylmethyl;

a "cyclic radical" is a condensed or noncondensed, monocyclic or polycyclic, nonaromatic cycloalkyl radical containing from 5 to 22 carbon atoms, possibly comprising one or more unsaturations; in particular, the cyclic radical is a cyclohexyl;

a "sterically hindered cyclic" radical is a substituted or unsubstituted, aromatic or nonaromatic, cyclic radical hindered by steric effect or constraint, comprising from 6 to 14 members, which may be bridged; by way of sterically hindered radicals, mention may be made of bicyclo[1.1.0]butane, mesityls such as 1,3,5-trimethylphenyl, 1,3,5-tri-tert-butylphenyl, 1,3,5-isobutylphenyl, 1,3,5-trimethylsilylphenyl and adamantyl;

a "heterocyclic radical or heterocycle" is a condensed or noncondensed, monocyclic or polycyclic, nonaromatic radical containing from 5 to 22 members, comprising from 1 to 6 heteroatoms chosen from nitrogen, oxygen, sulfur and selenium;

an "alkyl radical" is a linear or branched, $C_1$-$C_{16}$, preferably $C_1$-$C_8$, hydrocarbon-based radical;

the expression "optionally substituted" assigned to the alkyl radical implies that said alkyl radical may be substituted with one or more radicals chosen from the radicals: i) hydroxyl; ii) $C_1$-$C_4$ alkoxy; iii) acylamino; iv) amino optionally substituted with one or two $C_1$-$C_4$ alkyl radicals, which may be identical or different, said alkyl radicals possibly forming, with the nitrogen atom which bears them, a heterocycle comprising from 5 to 7 members, optionally comprising another heteroatom which may or may not be different from nitrogen; v) or a quaternary ammonium group —N$^+$R'R''R''', M for which R', R'', R''', which may be identical or different, represent a hydrogen atom or a $C_1$-$C_4$ alkyl group, or else —N$^+$R'R''R''' forms a heteroaryl such as imidazolium optionally substituted with a $C_1$-$C_4$ alkyl group, and M$^-$ represents the counterion of the corresponding organic acid, mineral acid or halide;

an "alkoxy radical" is an alkyloxy or alkyl-O-radical for which the alkyl radical is a linear or branched, $C_1$-$C_{16}$, preferably $C_1$-$C_8$, hydrocarbon-based radical;

an "alkylthio radical" is an alkyl-S— radical for which the alkyl radical is a linear or branched, $C_1$-$C_{16}$, preferably $C_1$-$C_8$, hydrocarbon-based radical; when the alkylthio group is optionally substituted, this implies that the alkyl group is optionally substituted as defined above;

an "alkylene chain" represents a divalent $C_1$-$C_{18}$ chain; in particular $C_1$-$C_6$, more particularly $C_1$-$C_2$ when the chain is linear; optionally substituted with one or more, identical or different, halogen atoms or groups chosen from hydroxyl, alkoxy, (di)(alkyl)amino and R$^a$—Z$^a$—C(Z$^b$)— with Z$^a$, Z$^b$, which may be identical or different, representing an oxygen or sulfur atom or a group NR$^{a'}$, and R$^a$ representing an alkali metal, a hydrogen atom or an alkyl group and R$^{a'}$ representing a hydrogen atom or an alkyl group;

a "saturated or unsaturated, optionally substituted $C_1$-$C_{30}$ hydrocarbon-based chain" represents a hydrocarbon-based, in particular $C_1$-$C_8$ chain, optionally comprising one or more π double bonds, which may or may not be conjugated, in particular the hydrocarbon-based chain is saturated; said chain is optionally substituted with one or more, identical or different, halogen atoms or groups chosen from hydroxyl, alkoxy, (di)(alkyl)amino and R$^b$—Z$^b$—C(Z$^c$)— with Z$^b$, Z$^c$, which may be identical or different, representing an oxygen or sulfur atom or a group NR$^{b'}$, and R$^b$ representing an alkali metal, a hydrogen atom or an alkyl group and R$^{b'}$ representing a hydrogen atom or an alkyl group;

the limits delimiting the extent of the range of values are included in this range of values;

an "organic or mineral acid salt" is more particularly chosen from a salt derived: i) from hydrochloric acid HCl; ii) from hydrobromic acid HBr; iii) from sulfuric acid $H_2SO_4$; iv) from alkylsulfonic acids: Alk-S(O)$_2$OH such as methylsulfonic acid and ethylsulfonic acid; v) from arylsulfonic acids: Ar—S(O)$_2$OH such as from benzenesulfonic acid and from toluenesulfonic acid; vi) from citric acid; vii) from succinic acid; viii) from tartaric acid; ix) from lactic acid; x) from alkoxysulfinic acids: Alk-O—S(O)OH such as from methoxysulfinic acid and from ethoxysulfinic acid; xi) from aryloxysulfinic acids such as from toluencoxysulfinic acid and from phenoxysulfinic acid; xii) from phosphoric acid $H_3PO_4$; xiii) from acetic acid $CH_3C(O)OH$; xiv) from triflic acid $CF_3SO_3H$ and xv) from tetrafluoroboric acid $HBF_4$;

an "anionic counterion" is an anion or an anionic group associated with the cationic charge of the dye; more particularly, the anionic counterion is chosen from: i) halides such as chloride or bromide; ii) nitrates; iii) sulfonates, among which are $C_1$-$C_6$ alkyl sulfonates: Alk-S(O)$_2$O$^-$ such as methyl sulfonate or mesylate and ethyl sulfonate; iv) aryl sulfonates: Ar—S(O)$_2$O$^-$ such as benzene sulfonate and toluenesulfonate or tosylate; v) citrate; vi) succinate; vii) tartrate; viii) lactate; ix) alkyl sulfates: Alk-O—S(O)O$^-$ such as methyl sulfate and ethyl sulfate; x) arylsulfates: Ar—O—S(O)O$^-$ such as benzenesulfate and toluenesulfate; xi) alkoxysulfates: Alk-O—S(O)$_2$O$^-$ such as methoxy sulfate and ethoxy sulfate; xii) aryloxysulfates: Ar—O—S(O)$_2$O$^-$; xiii) phosphate; xiv) acetate; xv) triflate; and xvi) borates such as tetrafluoroborate;

the "solvates" represent the hydrates and also the association with linear or branched $C_1$-$C_4$ alcohols such as ethanol, isopropanol or n-propanol.

The phenylpyrido[1,2-a]indolinium-derived disulfide or thiol fluorescent dyes of formula (I) as defined above are fluorescent dyes, i.e. are capable of absorbing in the UV radiation or visible range at a wavelength $\gamma_{abs}$ of between 250 and 800 nm and capable of re-emitting in the visible range at an emission wavelength $\gamma_{em}$ of between 400 and 800 nm.

Preferably, the fluorescent compounds of formula (I) of the invention are dyes capable of absorbing in the visible range $\gamma_{abs}$ of between 400 and 800 nm and of re-emitting in the visible range $\gamma_{em}$ of between 400 and 800 nm. More preferably, the dyes of formula (I) are dyes capable of absorbing at a $\gamma_{abs}$ of between 420 and 550 nm and of re-emitting in the visible range at a $\gamma_{em}$ of between 470 and 600 nm.

The compounds of the invention of formula (I) when n and m are 1, contain an SY function which may be in the covalent form —S—Y or ionic form —S$^-$Y$^+$ depending on the nature of Y and on the pH of the medium.

A specific embodiment relates to the phenylpyrido[1,2-a] indolinium-derived disulfide or thiol fluorescent dyes of formula (I) where n and m are 1 and Y represents a hydrogen atom or an alkali metal. Advantageously, Y represents a hydrogen atom.

In accordance with another specific embodiment of the invention, in the formula (I), Y is a protecting group known to those skilled in the art, for instance those described in the books "*Protective Groups in Organic Synthesis*", T. W. Greene, John Wiley & Sons Ed., NY, 1981, pp. 193-217; "*Protecting Groups*", P. Kocienski, Thieme, 3rd Ed., 2005, Chap. 5. It being understood that Y as protective group cannot constitute with the sulphur atom on which it is linked a disulfide dye i.e. cannot constitute a formula (I) in which n=m=1. Y as protective group cannot represent a group directly linked to the sulphur atom of formula (I) via another non oxidized sulphur atom.

Particularly when Y represents a thiol-function-protecting group, Y is chosen from the following radicals:

($C_1$-$C_4$)alkylcarbonyl;
($C_1$-$C_4$)alkylthiocarbonyl;
($C_1$-$C_4$)alkoxycarbonyl;
($C_1$-$C_4$)alkoxythiocarbonyl;
($C_1$-$C_4$)alkylthiothiocarbonyl;
(di)($C_1$-$C_4$)(alkyl)aminocarbonyl;
(di)($C_1$-$C_4$)(alkyl)aminothiocarbonyl;
arylcarbonyl such as phenylcarbonyl;
aryloxycarbonyl;
aryl($C_1$-$C_4$)alkoxycarbonyl;

(di)($C_1$-$C_4$) (alkyl)aminocarbonyl such as dimethyl-aminocarbonyl;

($C_1$-$C_4$)(alkyl)arylaminocarbonyl;

$SO_3^-$, $M^+$ with $M^+$ representing cationic counterion such as an alkali metal such as sodium or potassium, or else $An^-$ or $An'^-$ of formula (I) and $M^+$ are absent;

optionally substituted aryl such as phenyl, dibenzosuberyl or 1,3,5-cycloheptatrienyl;

optionally substituted heteroaryl; including in particular the cationic or noncationic heteroaryl comprising from 1 to 4 heteroatoms below:

i) monocyclic comprising 5, 6 or 7 members, such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium;

ii) bicyclic comprising 8 to 11 members, such as indolyl, indolinium, benzoimidazolyl, benzoimidazolium, benzoxazolyl, benzoxazolium, dihydrobenzoxazolinyl, benzothiazolyl, benzothiazolium, pyridoimidazolyl, pyridoimidazolium, thienocycloheptadienyl, these monocyclic or bicyclic groups being optionally substituted with one or more groups such as ($C_1$-$C_4$) alkyl, for instance methyl, or polyhalo($C_1$-$C_4$)alkyl, for instance trifluoromethyl;

iii) or tricyclic ABC below:

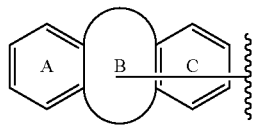

in which the two rings A, C optionally comprise a heteroatom, and the ring B is a 5-, 6- or 7-membered, particularly 6-membered ring and contains at least one heteroatom, for instance piperidyl or pyranyl;

optionally cationic, optionally substituted heterocycloalkyl, the heterocycloalkyl group represents in particular a saturated or partially saturated, 5-, 6- or 7-membered monocyclic group comprising from 1 to 4 heteroatoms chosen from oxygen, sulfur and nitrogen, such as di/tetrahydrofuranyl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidinyl, morpholinyl, di/tetra/hexahydroazepinyl or di/tetrahydropyrimidinyl, these groups being optionally substituted with one or more groups such as ($C_1$-$C_4$)alkyl, oxo or thioxo; or the heterocycle represents the following group:

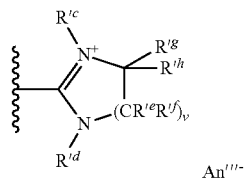

in which $R'^c$, $R'^d$, $R'^e$, $R'^f$, $R'^g$ and $R'^h$, which may be identical or different, represent a hydrogen atom or a ($C_1$-$C_4$)alkyl group, or else two groups $R'^g$ with $R'^h$, and/or $R'^e$ with $R'^f$, form an oxo or thioxo group, or else $R'^g$ with $R'^e$ together form a cycloalkyl; and v represents an integer between 1 and 3 inclusive; preferably, $R'^c$ to $R'^h$ represent a hydrogen atom; and $An'''^-$ represents a counterion;

—$C(NR'^cR'^d)=N^+R'^eR'^f$; $An'''^-$ with $R'^c$, $R'^d$, $R'^e$ and $R'^f$, which may be identical or different, representing a hydrogen atom or a ($C_1$-$C_4$)alkyl group; preferably, $R'^c$ to $R'^f$ represent a hydrogen atom; and $An'''^-$ represents a counterion;

—$C(NR'^cR'^d)=NR'^e$; with $R'^c$, $R'^d$ and $R'^e$ as defined above;

optionally substituted (di)aryl($C_1$-$C_4$)alkyl, such as 9-anthracenylmethyl, phenylmethyl or diphenylmethyl optionally substituted with one or more groups in particular chosen from ($C_1$-$C_4$) alkyl, ($C_1$-$C_4$)alkoxy such as methoxy, hydroxyl, alkylcarbonyl and (di)($C_1$-$C_4$) (alkyl)amino such as dimethylamino;

optionally substituted (di)heteroaryl($C_1$-$C_4$)alkyl, the heteroaryl group is in particular cationic or noncationic, and monocyclic, comprising 5 or 6 members and from 1 to 4 heteroatoms chosen from nitrogen, oxygen and sulfur, such as the groups pyrrolyl, furanyl, thiophenyl, pyridyl, pyridyl N-oxide such as 4-pyridyl or 2-pyridyl N-oxide, pyrylium, pyridinium or triazinyl, optionally substituted with one or more groups such as alkyl, (di)heteroaryl ($C_1$-$C_4$)alkyl is (di)heteroarylmethyl or (di)heteroarylethyl;

$CR^1R^2R^3$ with $R^1$, $R^2$ and $R^3$, which may be identical or different, representing a halogen atom or a group chosen from:

($C_1$-$C_4$)alkyl;

($C_1$-$C_4$)alkoxy;

optionally substituted aryl, such as phenyl optionally substituted with one or more groups such as ($C_1$-$C_4$) alkyl, ($C_1$-$C_4$)alkoxy or hydroxyl;

optionally substituted heteroaryl, such as thiophenyl, furanyl, pyrrolyl, pyranyl or pyridyl, optionally substituted with a ($C_1$-$C_4$)alkyl group;

$P(Z^1)R'^1R'^2R'^2$ with $R'^1$ and $R'^2$, which may be identical or different, representing a hydroxyl, ($C_1$-$C_4$)alkoxy or alkyl group, $R'^3$ representing a hydroxyl or $(C_1-C_4)$ alkoxy group and $Z^1$ representing an oxygen or sulfur atom;

a sterically hindered cyclic; and optionally substituted alkoxyalkyl, such as methoxymethyl (MOM), ethoxyethyl (EOM) or isobutoxymethyl.

According to a specific embodiment, the protected thiol dyes of formula (I) for which m and n are 1 comprise a group Y i) which is a cationic, aromatic 5- or 6-membered monocyclic heteroaryl group comprising from 1 to 4 heteroatoms chosen from oxygen, sulfur and nitrogen, such as oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinyl, pyrazinium, pyridazinium, triazinium, tetrazinium, oxazepinium, thiepinyl, thiepinium or imidazolium; ii) cationic 8- to 11-membered bicyclic heteroaryl group, such as indolinium, benzoimidazolium, benzoxazolium or benzothiazolium, these monocyclic or bicyclic heteroaryl groups being optionally substituted with one or more groups such as alkyl, for instance methyl, or polyhalo$(C_1-C_4)$alkyl, for instance trifluoromethyl; iii) or heterocyclic group below:

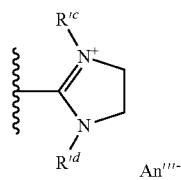

in which $R'^c$ and $R'^d$, which may be identical or different, represent a hydrogen atom or a $(C_1-C_4)$alkyl group; preferably, $R'^c$ to $R'^d$ represent a $(C_1-C_4)$alkyl group such as methyl; and $An'''^-$ represents an anionic counterion.

In particular, Y represents a group chosen from oxazolium, isoxazolium, thiazolium, isothiazolium, 1,2,4-triazolium, 1,2,3-triazolium, 1,2,4-oxazolium, 1,2,4-thiadiazolium, pyrylium, pyridinium, pyrimidinium, pyrazinium, pyridazinium, triazinium and imidazolium, benzoimidazolium, benzoxazolium, benzothiazolium, these groups being optionally substituted with one or more $(C_1-C_4)$alkyl groups, in particular methyl.

In particular, Y represents an alkali metal or a protecting group such as:

$(C_1-C_4)$alkylcarbonyl, such as methylcarbonyl or ethylcarbonyl;

arylcarbonyl such as phenylcarbonyl;

$(C_1-C_4)$alkoxycarbonyl;

aryloxycarbonyl;

aryl$(C_1-C_4)$alkoxycarbonyl;

(di)$(C_1-C_4)$ (alkyl)aminocarbonyl such as dimethylaminocarbonyl;

$(C_1-C_4)$ (alkyl)arylaminocarbonyl;

optionally substituted aryl, such as phenyl;

5- or 6-membered monocyclic heteroaryl, such as imidazolyl or pyridyl;

5- or 6-membered cationic monocyclic heteroaryl, such as pyrylium, pyridinium, pyrimidinium, pyrazinium, pyridazinium, triazinium or imidazolium; these groups being optionally substituted with one or more identical or different $(C_1-C_4)$alkyl groups, such as methyl;

8- to 11-membered cationic bicyclic heteroaryl, such as benzoimidazolium or benzoxazolium; these groups being optionally substituted with one or more identical or different $(C_1-C_4)$alkyl groups, such as methyl;

cationic heterocycle of the following formula:

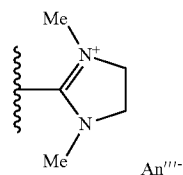 [SMILES: *C1=[N+](C)CCN1C]

isothiouronium —$C(NH_2)$=$N^+H_2$; $An''''^-$;

isothiourea —$C(NH_2)$=NH;

$SO_3^-$, $M^+$ with $M^+$ representing a cationic counterion such as an alkali metal such as sodium or potassium, or else $An^-$ or $An'^-$ of formula (I) and $M^+$ are absent.

According to a specific embodiment of the invention, the fluorescent dyes of formula (I) are disulfide dyes with n=2 and m=0.

In particular, the fluorescent dyes of the invention are of formula (Ia):

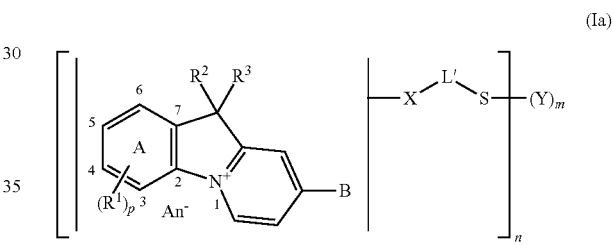

in which formula (Ia):

m, n, p, $R^1$, B and Y are as defined above;

X represents a radical chosen from: -G-, -G'-C(G)- and —C(G)-G'-, with G and G', which may be identical or different, representing an oxygen or sulfur atom or NR, with R representing a hydrogen atom or a $(C_1-C_6)$alkyl group, advantageously X represents a group —NR—, —NR—CO— or —C(O)—NR—; X is linked to the rest of the molecule by A or B; preferably at position 5 on A or in the para-position with respect to B when B represents a phenyl group; when B represents an indolyl group, then X represents a σ bond and L' is directly linked to the nitrogen of the indole ring;

L' represents a saturated, hydrocarbon-based $C_2-C_8$ alkylene chain, optionally interrupted with a group chosen from —N($R'_a$)—; —$N^+$($R'_a$)($R'_b$)—, $An^-$; —C(O)—N($R'_a$)— and —N($R'_a$)—C(O)—, or a divalent cationic heteroaryl comprising from 5 to 7 members, such as imidazolium, with $R'_a$, $R'_b$, which may be identical or different, representing a hydrogen atom or a $(C_1-C_6)$ alkyl radical, and $An^-$ representing an anionic counterion; in particular, L' is an uninterrupted $C_2-C_6$ alkylene chain such as ethylene;

$R^2$ and $R^3$, which may be identical or different, represent a $C_1-C_3$ alkyl group; in particular, $R^2$ and $R^3$ are identical and represent a methyl group.

By way of example, mention may be made of the following fluorescent dyes of formula (I):

1
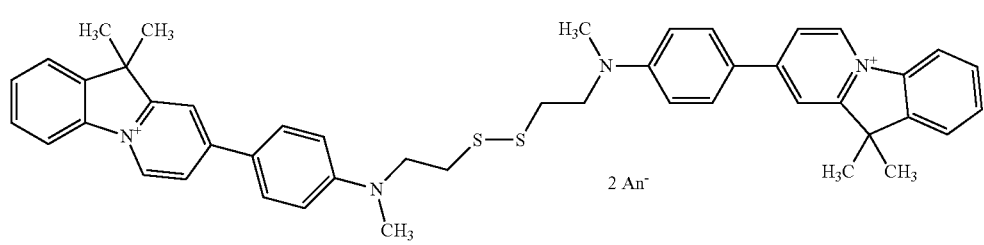
2
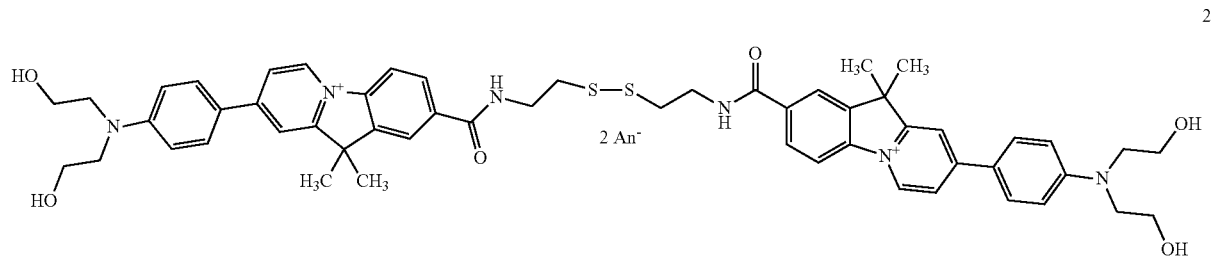
3
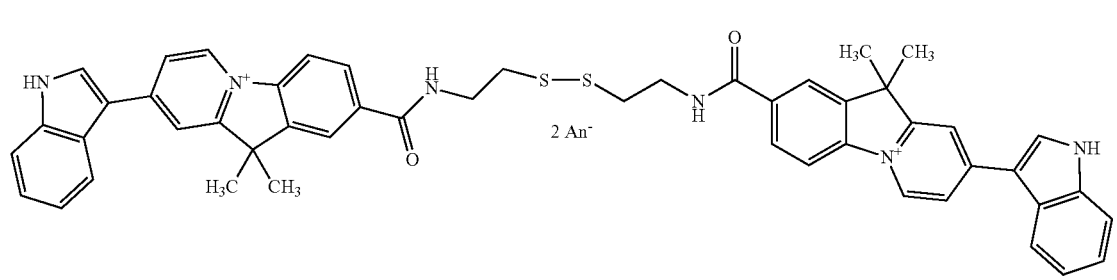
4
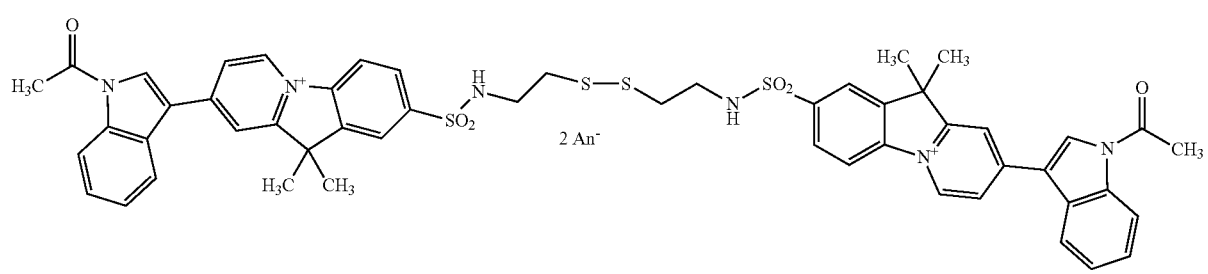
5
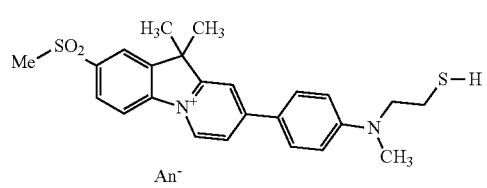
6
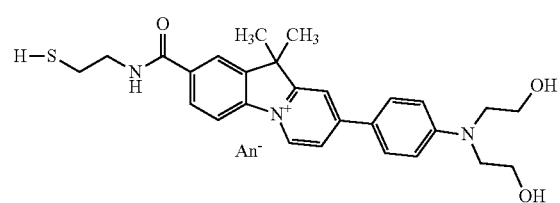
7
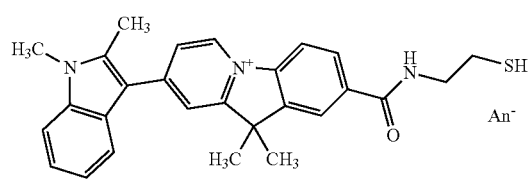
8
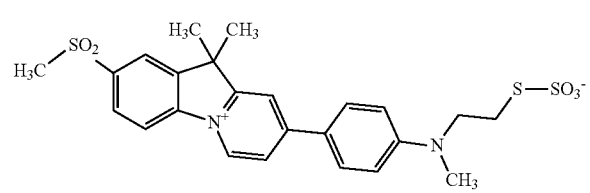

-continued
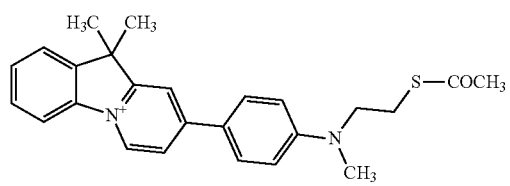
9
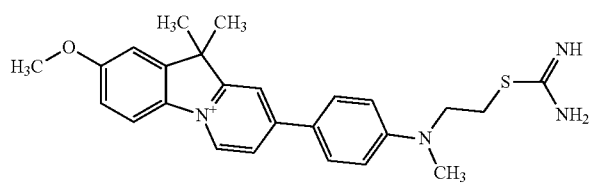
10
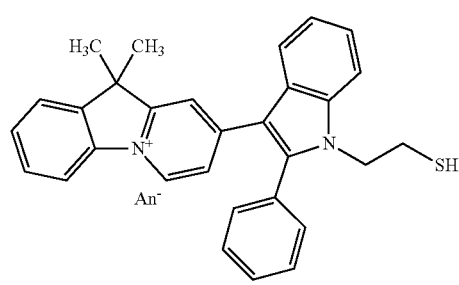
11
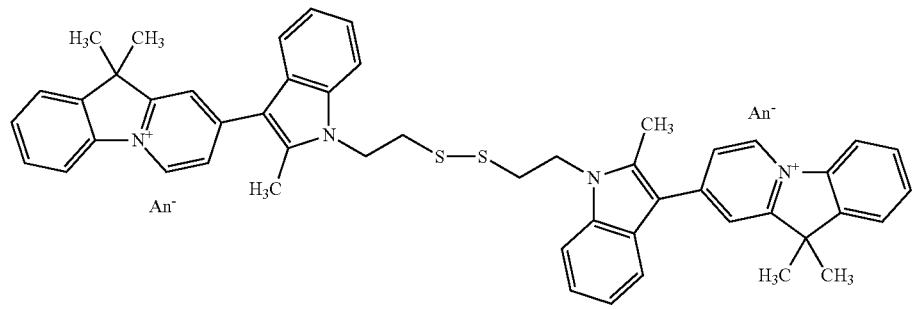
12
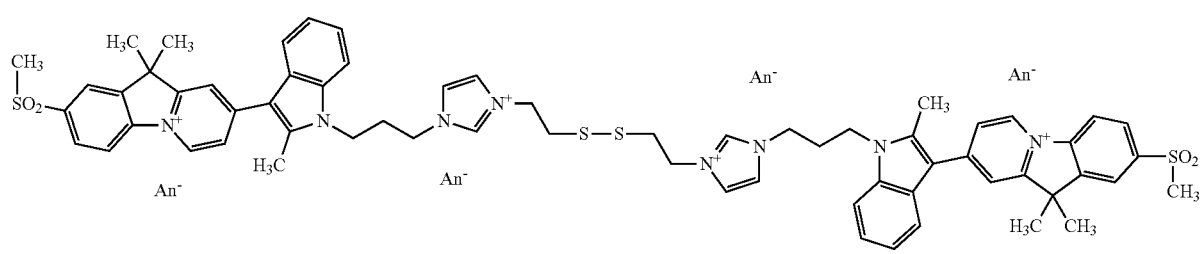
13
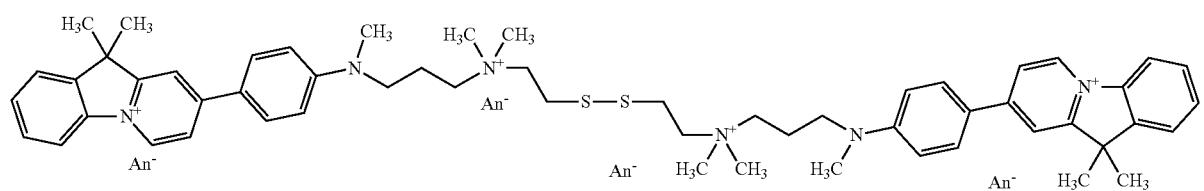
14
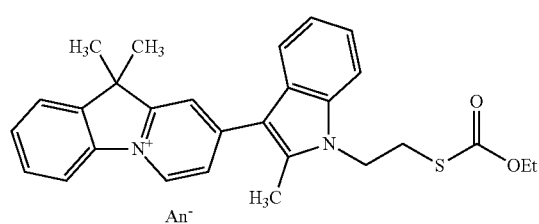
15

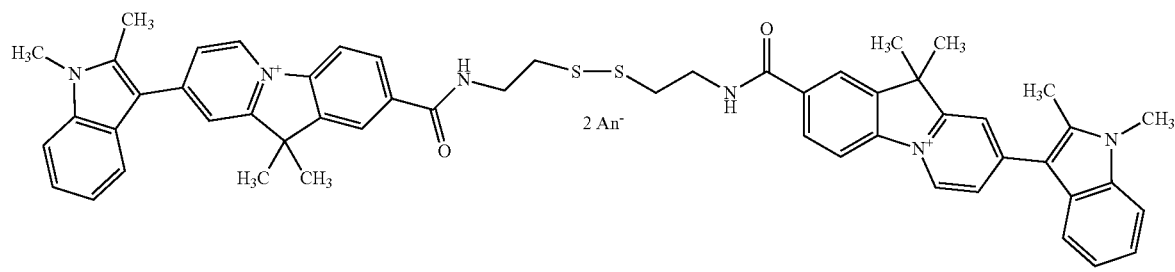

16

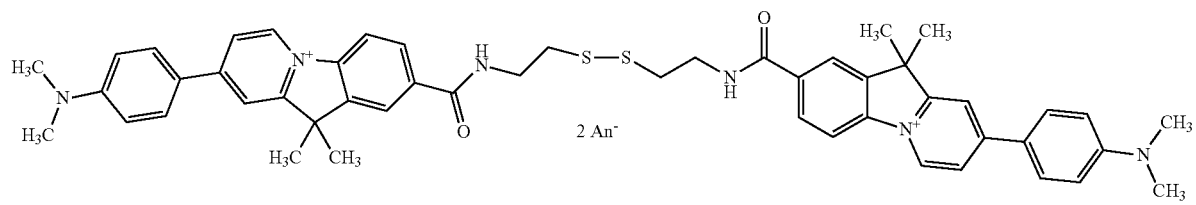

17

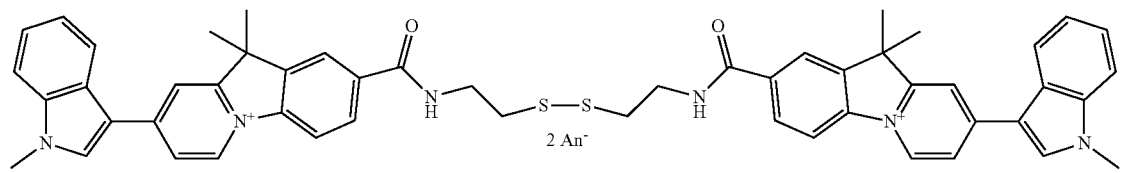

18 with An⁻, which may be identical or different, representing an anionic counterion.

For all the exemplary embodiments, which follow, of preparation of the novel phenylpyrido[1,2-a]indolinium-derived disulfide or thiol fluorescent dyes of formula (I), those skilled in the art know how to pre-protect the reactive functions such as ketone functions of the chromophore and then to deprotect them for the needs of the synthesis reaction, by the known conventional methods of protection/deprotection such as those described in the books mentioned above by T.W Greene John Willey & Sons ed., NY, 1981, or P. Kocienski "Protecting Groups", P. Kocienski, Thieme, 3rd ed., 2005.

The protected thiol fluorescent dyes of formula (I-Y) for which m and n are 1 can be synthesized in two stages. The first stage consists in preparing the nonprotected thiol dye (1-H) according to the methods known to those skilled in the art, for instance "*Thiols and organic sulfides*", "*Thiocyanates and isothiocyanates, organic*", Ullmann's Encyclopedia, Wiley-VCH, Weinheim, 2005. In addition, the second step consists in protecting the thiol function according to the conventional methods known to those skilled in the art in order to produce the protected thiol dyes of formula (I-Y). By way of example, for protecting the thiol function —SH of the thiol dye, use may be made of the methods in the books "*Protective Groups in Organic Synthesis*", T. W. Greene, John Willey & Sons Ed., NY, 1981, pp. 193-217; "*Protecting Groups*", P. Kocienski, Thieme, 3rd Ed., 2005, Chap. 5. This method can be illustrated by means of the method consisting i) in generating phenylpyrido[1,2-a]indolinium-derived thiol fluorescent dyes of formula (I-H) by reduction of a two-chromophore phenylpyrido[1,2-a]indolinium-derived fluorescent dye bearing a disulfide function —S—S— such as (I-S) and ii) in protecting said thiol function of (I-H), according to the conventional methods, with the reactant 7 Y'R in order to obtain the protected thiol dyes of formula (I-Y). The thiol compound (I-H) may also be metallated with an alkali metal or alkaline earth metal Met* so as to produce the thiolate fluorescent dye of formula (I-Met) or (II-Met).

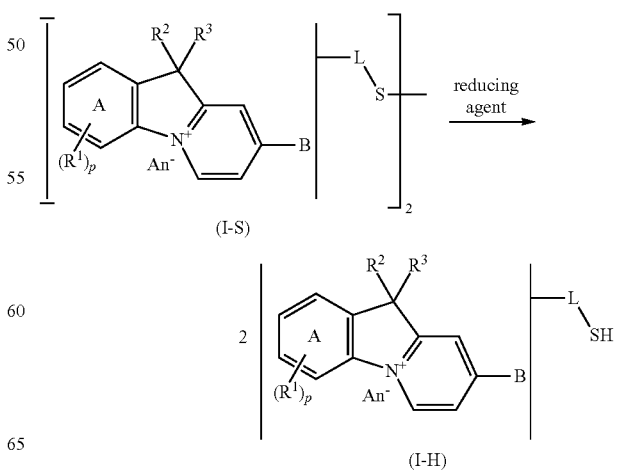

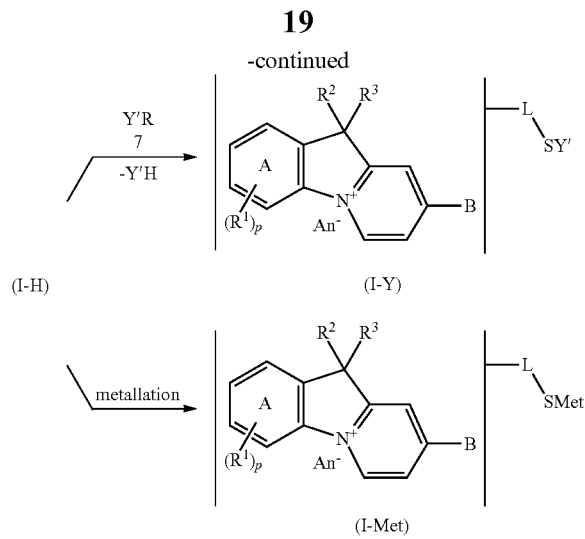

(I-H)   (I-Y)

(I-Met)

with Y' representing a thiol-function-protecting group; Met* representing an alkali metal or an alkaline earth metal, particularly sodium or potassium, it being understood that, when the metal is an alkaline earth metal, 2 chromophores comprising a thiolate —S⁻ function can be associated with 1 Metal$^{2+}$; and with p, q, $R^1$ to $R^3$, B, An⁻ and L being as defined above; Y' represents a thiol-function-protecting group; and R represents a nucelofuge leaving group, for instance mesylate, tosylate, triflate or halide.

According to another possibility, a protected thiol compound (b) protected with a protecting group Y' as defined above, prepared according to one of the procedures described in the books described above, said protected thiol compound comprising at least one nucleophilic function, can be reacted with a sufficient, preferably equimolar, amount of a phenylpyrido[1,2-a]indolinium-derived chromophore (a) and which comprises an electrophilic function so as to form a Σ covalent bond; see below in the preparation of dyes of formula (I'-Y):

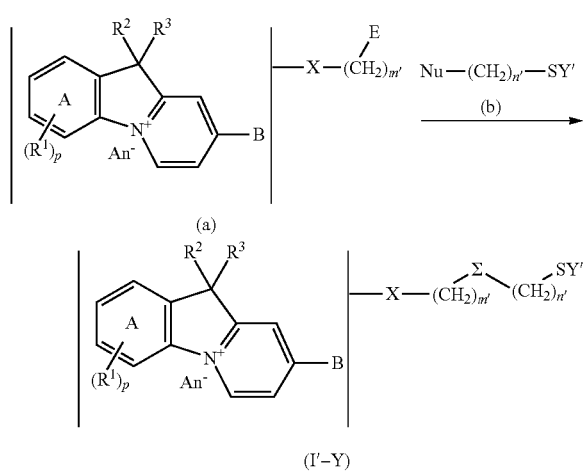

(a)

(I'-Y)

with p, $R^1$ to $R^3$, B, An⁻ and X as defined above; m' and n' are integers between 1 and 6 with m'+n' being an integer between 2 and 6; Nu representing a nucleophilic group; E representing an electrophilic group; and Σ the linking group generated after attack by the nucleophile on the electrophile.

By way of example, the Σ covalent bonds that can be generated are listed in the table below based on condensation of electrophiles with nucleophiles:

| Electrophiles E | Nucleophiles Nu | Σ Covalent bonds |
|---|---|---|
| Activated esters* | Amines | Carboxamides |
| Acyl nitrides** | Amines | Carboxamides |
| Acyl halides | Amines | Carboxamides |
| Acyl halides | Alcohols | Esters |
| Acyl cyanides | Alcohols | Esters |
| Acyl cyanides | Amines | Carboxamides |
| Alkyl halides | Amines | Alkylamines |
| Alkyl halides | Carboxylic acids | Esters |
| Alkyl halides | Thiols | Thioesters |
| Alkyl halides | Alcohols | Ethers |
| Sulfonic acids and salts thereof | Thiols | Thioethers |
| Sulfonic acids and salts thereof | Carboxylic acids | Esters |
| Sulfonic acids and salts thereof | Alcohols | Ethers |
| Anhydrides | Alcohols | Esters |
| Anhydrides | Amines | Carboxamides |
| Aryl halides | Thiols | Thioethers |
| Aryl halides | Amines | Arylamines |
| Aziridines | Thiols | Thioethers |
| Carboxylic acids | Amines | Carboxamides |
| Carboxylic acids | Alcohols | Esters |
| Carbodiimides | Carboxylic acids | N-acylureas |
| Diazoalkanes | Carboxylic acids | Esters |
| Epoxides | Thiols | Thioethers |
| Haloacetamides | Thiols | Thioethers |
| Imide esters | Amines | Amidines |
| Isocyanates | Amines | Ureas |
| Isocyanates | Alcohols | Urethanes |
| Isothiocyanates | Amines | Thioureas |
| Maleimides | Thiols | Thioethers |
| Sulfonic esters | Amines | Alkylamines |
| Sulfonic esters | Thiols | Thioethers |
| Sulfonic esters | Carboxylic acids | Esters |
| Sulfonic esters | Alcohols | Ethers |
| Sulfonyl halides | Amines | Sulfonamides |

*the activated esters of general formula —CO-Part with Part representing a leaving group such as oxysuccinimidyl, oxybenzotriazolyl, aryloxy which is optionally substituted;
**the acyl nitrides may rearrange to give isocyanates.

A variant to this process is to use a phenylpyrido[1,2-a]indolinium chromophore having an electrophilic acrylate function (—OCO—C═C—) on which is carried out an addition reaction that will generate a E bond.

It is also possible to use a thiol reactant (α): Y'—SH comprising a Y' group as defined above, the nucleophilic SH function of which can react with the carbon atom of the radical in the α-position with respect to the halogen atom borne by a phenylpyrido[1,2-a]indolinium-derived chromophore of (a'), so as to give the protected thiol dye of formula (I-Y) as defined above:

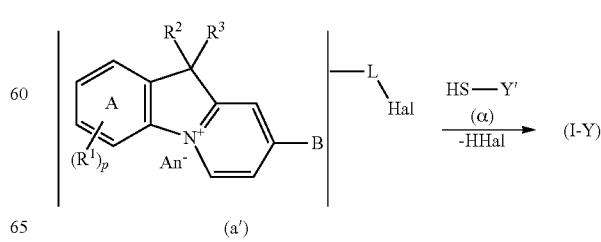

(a')

with p, $R^1$ to $R^3$, B, $An^-$ and (I-Y) as defined above, and Hal representing a nucleofuge halogen atom such as bromine, iodine or chlorine.

More particularly, a nucleofuge leaving group may be replaced with a derivative of a thiourea (S=C(NRR)NRR) so as to generate isothiouroniums. For example, based on chromophores (a') as defined above if the thiourea group is a thioimidazolium (β), so as to give the dye which is S-protected with an imidazolium group (I"-Y):

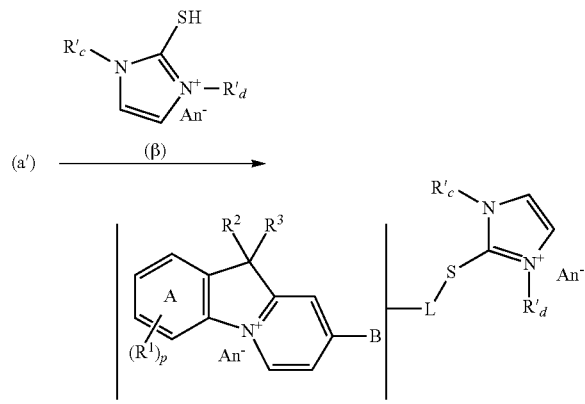

with p, $R^1$ to $R^3$, B, $An^-$, (e), $R'_c$ and $R'_d$ as defined above.

Another variant may make it possible to obtain the compound (I"-Y) using the cyclic thiourea of imidazole type (b'), followed by alkylation of said imidazole using $R'_d$-Lg, with Lg being a leaving group such as chloride, bromide, tosylate or mesylate:

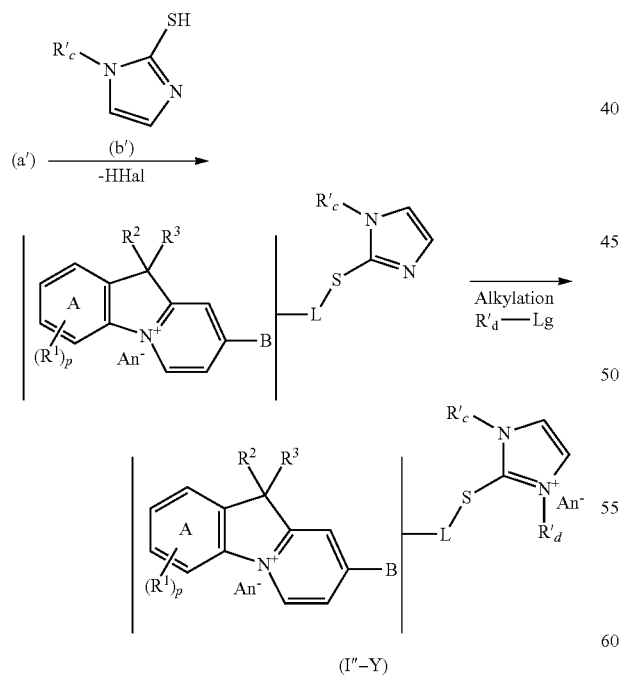

with p, $R^1$ to $R^3$, B, $An^-$, (a') $R'_c$, $R'_d$ and Lg as defined above.

A variant is to use, in place of the halide comprising the fluorescent chromophore (a'), a chromophore comprising another type of nucleofuge such as tosylate or mesylate.

In accordance with another possibility, certain protected thiol dyes (I'-Y) can be obtained by reacting a protected thiol compound with a compound bearing two carboxylic acid functions that are activated, according to the conventional methods (for example, reaction with a carbodiimide or with thionyl chloride). The resulting product (d) is subsequently reacted with a phenylpyrido[1,2-a]indolinium-derived chromophore (c) bearing a nucleophilic function, for example of primary or secondary amine type, or of aliphatic alcohol type.

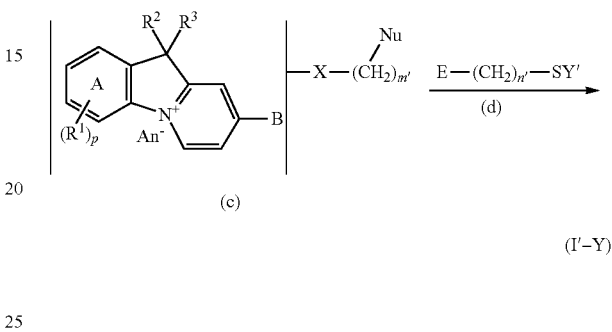

with p, $R^1$ to $R^3$, B, An, X, E, Nu, (I'-Y) as defined above.

Another variant is to use a thiolactone derivative based on specific nucleophilic chromophores (c') so as to give the derivatives (I'-H) comprising a linker L' interrupted with an amide function as represented by the scheme below:

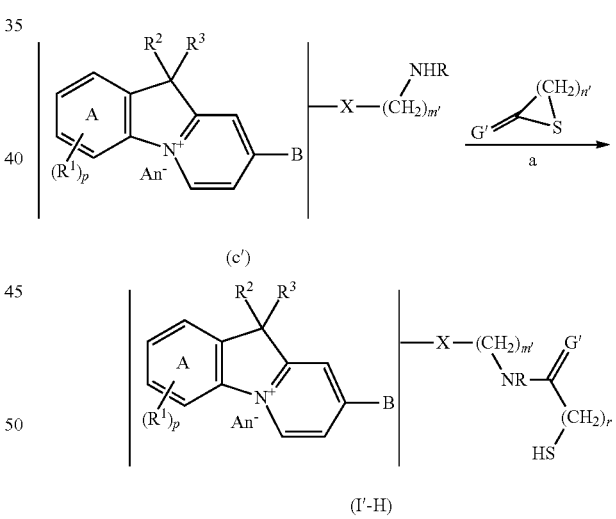

with p, $R^1$ to $R^3$, B, $An^-$, X, m' and n' as defined above, G' representing an oxygen or sulfur atom or an NR' group with R' representing a hydrogen atom or a alkyl radical, and R representing a hydrogen atom, a $C_1$-$C_4$ alkyl radical, a $C_1$-$C_4$ hydroxyalkyl radical or an aryl($C_1$-$C_4$)alkyl. The thiolactone derivative is preferably chosen with n'=3 and G' represents an oxygen atom.

The derivatives (I'-H) comprising a free SH function can then be protected or metallated as seen above.

In accordance with another possibility, the protected thiol dyes of formula (I''-Y) can be obtained by reaction of a compound (d') comprising a thiol group protected with a Y' group, and a nucleofuge leaving group Lg, for instance mesylate, tosylate, triflate or halide, with a phenylpyrido[1,2-a]indolinium-derived chromophore (c').

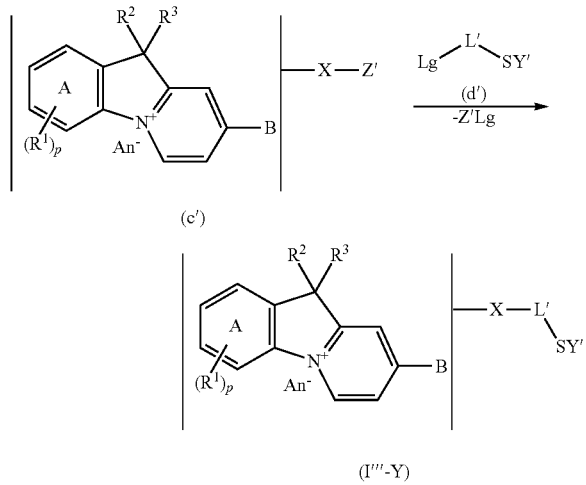

with p, $R^1$ to $R^3$, B, $An^-$, X, L' and Y' as defined above and Z' represents a hydrogen atom or a group activating the nucleophilicity of X.

By way of example, a compound containing a protected thiol group (I'''-Y) contains a nucleofuge leaving group R, for instance mesylate, tosylate or triflate, which can undergo nucleophilic attack from the amine borne by the hemicyanin styryl chromophore (c') as

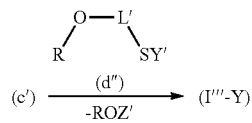

Reference may be made to the book *Advanced Organic Chemistry*, "Reactions, Mechanisms and Structures", J. March, 4th Ed., John Willey & Sons, 1992 or T. W. Greene "*Protective Groups in Organic Synthesis*", for further details on the operating conditions used for the processes mentioned above.

The phenylpyrido[1,2-a]indolinium-derived thiol fluorescent dyes of formula (I) with n=1 and m=1 formed can be converted to —SY' protected thiol fluorescent dyes by protection of the —SH thiol using the conventional protecting groups. The thiol dyes are metallated by also using the conventional methods known to those skilled in the art, such as those described in *Advanced Organic Chemistry*, "Reactions, Mechanisms and Structures", J. March, 4th Ed., John Willey & Sons, NY, 1992.

The phenylpyrido[1,2-a]indolinium-derived protected thiol fluorescent dyes of formula (I) can be deprotected by conventional pathways such as those described in the books "*Protective Groups in Organic Synthesis*", T. W. Greene, John Willey & Sons Ed., NY, 1981; "*Protecting Groups*", P. Kocienski, Thieme, 3rd Ed., 2005.

The starting reactants are commercially available or accessible by conventional methods known to those skilled in the art.

The disulfide fluorescent dyes of formula (I-S) can be synthesized in two stages. The first stage consists in preparing the nonprotected thiol dye (I-H) according to the methods known to those skilled in the art and described above. In addition, the second step consists in oxidizing the thiol function according to the conventional methods known to those skilled in the art, so as to give the disulfide dyes (I-S). By way of example for oxidizing the thiol function —SH of the thiol dye, use may be made of the methods in the books "*Protective Groups in Organic Synthesis*", T. W. Greene, John Willey & Sons ed., NY, 1981, pp. 193-217; "*Protecting Groups*", P. Kocienski, Thieme, 3rd ed., 2005.

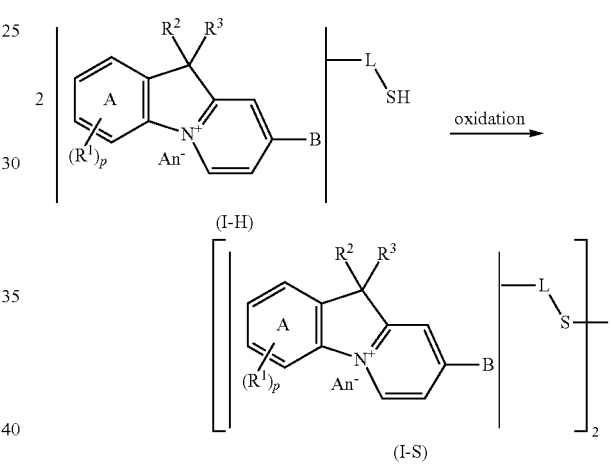

The oxidizing agent is chosen from an oxidase, among which mention may be made of peroxidases, 2-electron oxidoreductases such as uricases, and 4-electron oxygenases such as laccases, $O_2$, $Na_2O$, $KMnO_4$, $K_3Fe(CN)_6$, $MnO_2$, $H_2O_2$, $Ag_2O$, $AgO$, $NiO_2$, $NaBO_3$, $Na_2S_2O_8$, $CH_3CO_3H$, $C_6H_5CO_3H$, CuX (X=Br, Cl) $CuSO_4$, $(NH_4)_2Ce (NO_3)_6$, $PbO_2$, $Pb(OCOCH_2)_4$, $SeO_2$, $CrO_3.2C_5H_4N$ and NaOCl. The preferred oxidants will be chosen from $KMnO_4$, $K_3Fe(CN)_6$, $MnO_2$, $H_2O_2$, CuX (X=Br, Cl), $CuSO_4$, $Pb(OCOCH_2)_4$ and NaOCl. In addition, preferably, the preferential oxidizing agents will be chosen from $K_3Fe(CN)_6$, $MnO_2$, $H_2O_2$, CuBr and NaOCl. The reaction is preferably carried out at a temperature of between 0° C. and 40° C. in a solvent which is preferably polar, chosen from water, which is in particular aliphatic comprising up to 4 carbon atoms, dimethylformamide, dimethyl sulfoxide, acetonitrile, N-methylpyrrolidone, 1,3-dimethyl-2-oxohexahydro-pyrimidine (DMPU) at a pH of between 5 and 9.5.

In accordance with another possibility, the disulfide dyes of formula (I'-S) can be obtained by reaction of a disulfide compound (e) comprising a cinnamaldehyde group and a 2,3,3-trimethyl-3H-indolinium compound (f).

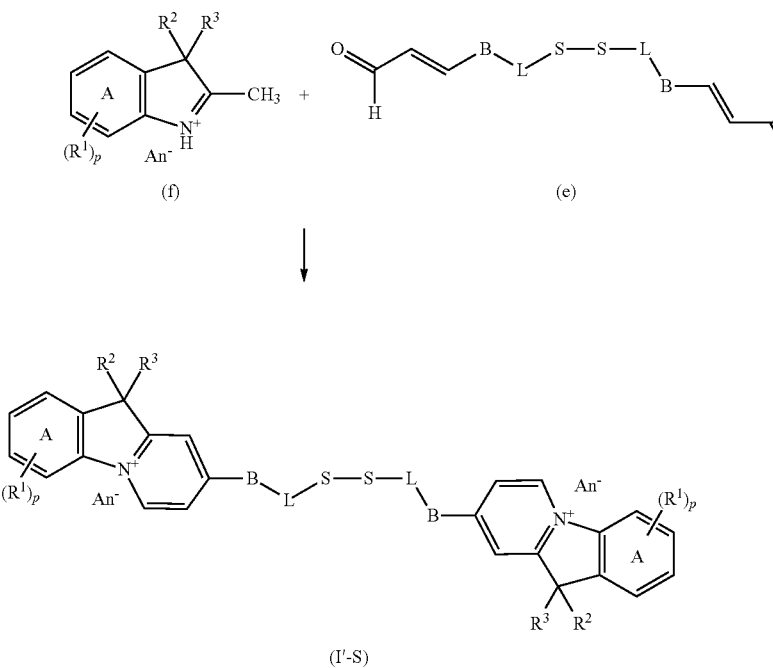

(f) + (e)

(I'-S)

with p, $R^1$ to $R^3$, B, $An^-$ and L as defined above. Mention may be made of the publications Khimiya Geterotsiklicheskikh Soedinenii (1987), 4, 481-3 and Youji Huaxue (1991), 11(2), 214-218 for the reaction conditions.

According to another possibility, a disulfide compound comprising two nucleophilic functions (g) as defined above, prepared according to one of the procedures described in the books cited above, can be reacted with a sufficient amount of a phenylpyrido[1,2-a]indolinium-derived chromophore (a), and which comprises an electrophilic function, so as to form a E covalent bond; see below, the preparation of dyes of formula (I''-S):

with p, $R^1$ to $R^3$, B, $An^-$, m', n', Nu, Σ, E and X as defined above.

In accordance with another possibility, some disulfide dyes (I''-S) can be obtained by reacting a disulfide compound (h) bearing two electrophilic functions with a phenylpyrido[1,2-a]indolinium-derived chromophore (a) bearing a nucleophilic function, for example of primary or secondary amine type, or of aliphatic alcohol type.

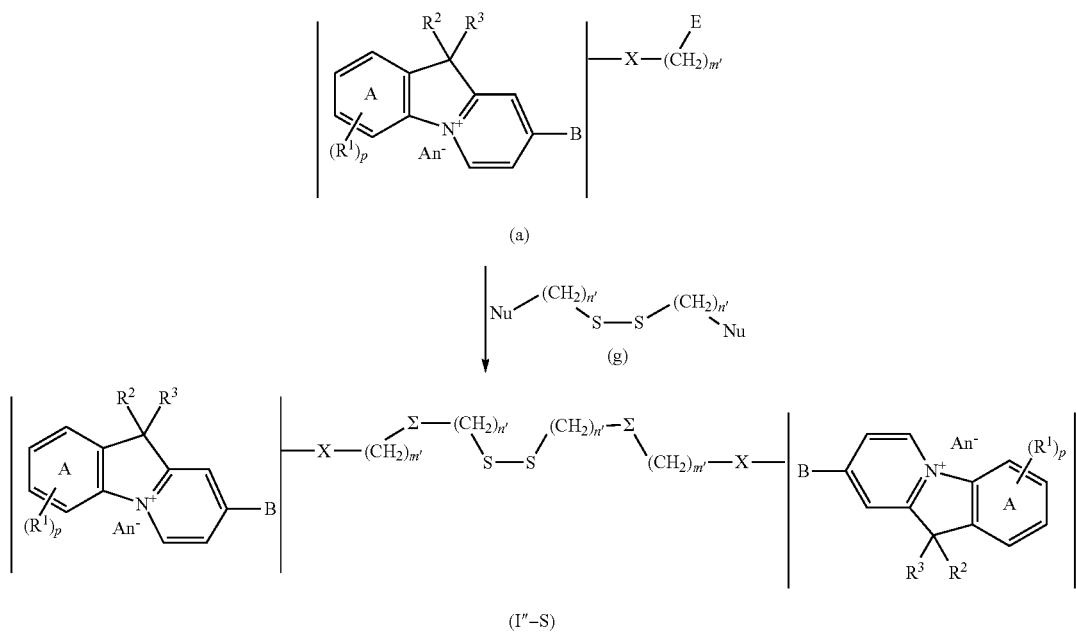

(a)

(g)

(I''-S)

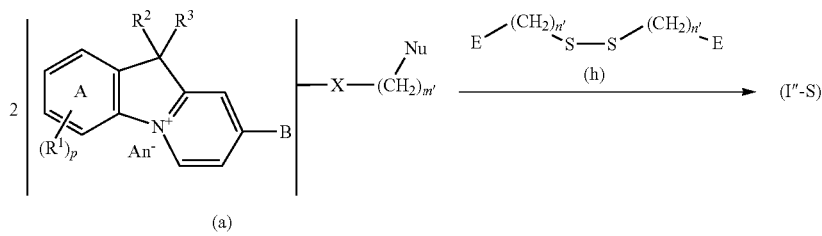

(a)

with p, $R^1$ to $R^3$, B, $An^-$, X, E, Nu and (I″-S) as defined above.

In accordance with an alternative, the disulfide dyes (I‴-S) comprising an indole unit (B is an indolyl group) can be obtained by reaction of a compound (a″) comprising a group Z′ with a disulfide compound (h) bearing two electrophilic functions.

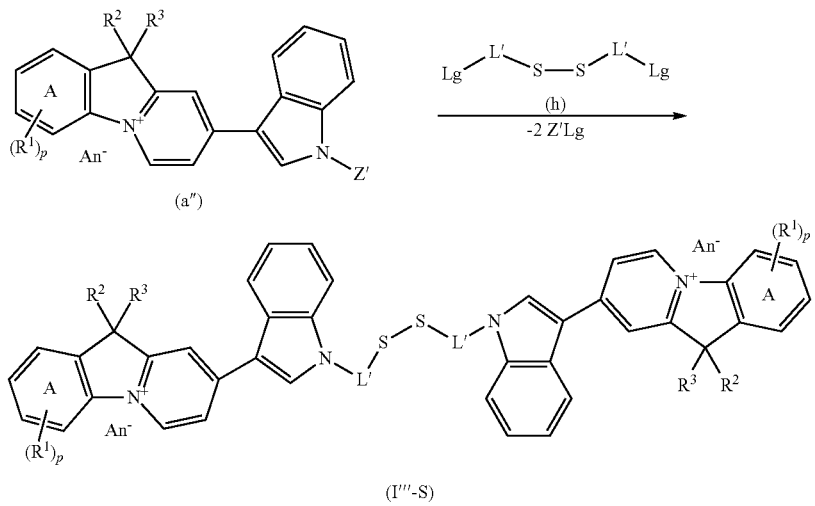

with p, $R^1$ to $R^3$, $An^-$, Lg, Z′, L′ and Y′ as defined above.

Reference may be made to the book *Advanced Organic Chemistry*, "Reactions, Mechanisms and Structures", J. March, 4th Ed., John Willey & Sons, 1992 or T. W. Greene "*Protective Groups in Organic Synthesis*", for further details on the operating conditions used for the processes mentioned above.

The phenylpyrido[1,2-a]indolinium-derived thiol fluorescent dyes of formula (I) with n=1 and m=1 formed can be converted to —SY′ protected thiol dyes by protection of the —SH thiol using the conventional protecting groups. The thiol dyes are metallated by also using the conventional methods known to those skilled in the art, such as those described in *Advanced Organic Chemistry*, "Reactions, Mechanisms and Structures", J. March, 4th Ed., John Willey & Sons, NY, 1992.

The phenylpyrido[1,2-a]indolinium-derived protected thiol dyes of formula (I) can be deprotected by conventional pathways such as those described in the books "*Protective Groups in Organic Synthesis*" T. W. Greene, John Willey & Sons Publisher, NY, 1981; "*Protecting Groups*", P. Kocienski, Thieme, 3rd Ed., 2005.

The starting reactants are commercially available or accessible by conventional methods known to those skilled in the art.

Another subject of the invention is a composition containing at least one phenylpyrido[1,2-a]indolinium-derived disulfide, thiol or protected thiol fluorescent dye of formula (I). In addition to the presence of at least one fluorescent dye of formula (I), the composition of the invention may also contain a reducing agent.

This reducing agent may be chosen from thiols, for example cysteine, homocysteine or thiolactic acid, the salts of these thiols, phosphines, bisulfite, sulfites, thioglycolic acid, and also its esters, in particular glyceryl monothioglycolate, and thioglycerol. This reducing agent may also be chosen from borohydrides and derivatives thereof, for instance the salts of borohydride, of cyanoborohydride, of triacetoxyborohydride or of trimethoxyborohydride: sodium salts, lithium salts, potassium salts, calcium salts, quaternary ammonium (tetramethylammonium, tetraethylammonium, tetra-n-butylammonium or benzyltriethylammonium) salts; and catechol borane.

The dye composition that can be used in the invention generally contains an amount of dye of formula (I) of between 0.001% and 50% relative to the total weight of the composition. Preferably, this amount is between 0.005% and 20% by weight, and even more preferably between 0.01% and 5% by weight, relative to the total weight of the composition.

The dye composition may also contain additional direct dyes. These direct dyes are, for example, chosen from neutral, acidic or cationic nitrobenzene direct dyes, neutral, acidic or cationic azo direct dyes, tetraazapentamethine dyes, neutral, acidic or cationic quinone, in particular anthraquinone dyes, azine direct dyes, triarylmethane direct dyes, indoamine direct dyes and natural direct dyes.

Among the natural direct dyes, mention may be made of lawsone, juglone, alizarin, purpurin, carminic acid, kermesic acid, purpurogallin, protocatechaldehyde, indigo, isatin, curcumin, spinulosin and apigenindin. Extracts or decoctions containing these natural dyes, and in particular poultices or henna-based extracts, may also be used.

The dye composition may contain one or more oxidation bases and/or one or more couplers conventionally used for dyeing keratin fibers.

Among the oxidation bases, mention may be made of para-phenylenediamines, bisphenylalkylenediamines, para-aminophenols, bis-para-aminophenols, ortho-aminophenols, heterocyclic bases, and addition salts thereof.

Among these couplers, mention may in particular be made of meta-phenylenediamines, meta-aminophenols, meta-diphenols, naphthalene couplers, heterocyclic couplers, and addition salts thereof.

The coupler(s) is (are) each generally present in an amount of between 0.001% and 10% by weight of the total weight of the dye composition, preferably between 0.005% and 6%.

The oxidation base(s) present in the dye composition is (are) in general each present in an amount of between 0.001% and 10% by weight of the total weight of the dye composition, preferably between 0.005% and 6% by weight.

In general, the addition salts of the oxidation bases and of the couplers that can be used in the context of the invention are in particular chosen from addition salts with an acid, such as hydrochlorides, hydrobromides, sulfates, citrates, succinates, tartrates, lactates, tosylates, benzenesulfonates, phosphates and acetates, and addition salts with a base, such as hydroxides of an alkali metal such as sodium or potassium, aqueous ammonia, amines or alkanolamines.

The cosmetic medium suitable for dyeing, also called dye support, is a cosmetic medium generally constituted of water or of a mixture of water and at least one organic solvent. By way of organic solvent, mention may, for example, be made of $C_1$-$C_4$ lower alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether, and also aromatic alcohols such as benzyl alcohol or phenoxyethanol, and mixtures thereof.

The solvents, when they are present, are preferably present in proportions of preferably between 1% and 40% by weight approximately, relative to the total weight of the dye composition, and even more preferably between 5% and 30% by weight approximately. The solvents, including water, are preferably present in proportions of preferably between 1% and 99% by weight approximately, relative to the total weight of the dye composition, and even more preferably between 5% and 95% by weight approximately.

The dye composition may also contain various adjuvants conventionally used in hair-dyeing compositions, such as anionic, cationic, nonionic, amphoteric or zwitterionic surfactants or mixtures thereof, anionic, cationic, nonionic, amphoteric or zwitterionic polymers, or blends thereof, mineral or organic thickeners, and in particular anionic, cationic, nonionic and amphoteric associative polymer thickeners, antioxidants, penetrating agents, sequestering agents, fragrances, buffers, dispersing agents, conditioning agents such as, for example, modified or unmodified, volatile or nonvolatile silicones, such as amino silicones, film-forming agents, ceramides, preservatives, opacifiers or conductive polymers.

The above adjuvants are in general present in an amount, for each of them, of between 0.01% and 20% by weight relative to the weight of the composition.

Of course, those skilled in the art will take care to select this or these possible additional compounds in such a way that the advantageous properties intrinsically associated with the dye composition in accordance with the invention are not, or are not substantially, impaired by the addition(s) envisaged.

The pH of the dye composition is generally between 3 and 14 approximately, and preferably between 5 and 11 approximately. It may be adjusted to the desired value by means of acidifying or basifying agents normally used in the dyeing of keratin fibers or else by means of conventional buffer systems.

Among the acidifying agents, mention may, by way of example, be made of mineral or organic acids, such as hydrochloric acid, orthophosphoric acid, sulfuric acid, carboxylic acids, for instance acetic acid, tartaric acid, citric acid or lactic acid, or sulfonic acids.

Among the basifying agents, mention may, by way of example, be made of aqueous ammonia, alkali carbonates, alkanolamines such as mono-, di- and triethanolamines, and also derivatives thereof, sodium hydroxide or potassium hydroxide and the compounds of formula (γ) below:

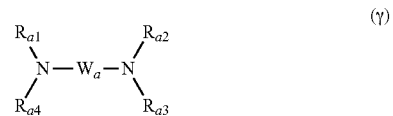

in which $W_a$ is a propylene residue optionally substituted with a hydroxyl group or a $C_1$-$C_4$ alkyl radical; $R_{a1}$, $R_{a2}$, $R_{a3}$ and $R_{a4}$, which may be identical or different, represent a hydrogen atom, a $C_1$-$C_4$ alkyl radical or a $C_1$-$C_4$ hydroxyalkyl radical.

The dye composition may be in various forms, such as in the form of a liquid, a cream or a gel, or in any other form suitable for dyeing keratin fibers, and in particular the hair.

Another subject of the invention is a process for dyeing keratin materials, in particular keratin fibers such as dark hair, consisting in applying a dye composition comprising, in a cosmetic medium, at least one phenylpyrido[1,2-a]indolinium-derived disulfide or thiol fluorescent dye of formula (I) as defined above to the keratin materials.

According to a specific embodiment, in the process of the invention, the reducing agent may be applied as a pretreatment before the application of the composition containing at least one phenylpyrido[1,2-a]indolinium-derived fluorescent dye of formula (I).

This pretreatment may be of short duration, in particular from 1 second to 30 minutes, preferably from minute to 15 minutes, with a reducing agent as mentioned above.

According to another process, the composition comprising at least one phenylpyrido[1,2-a]indolinium-derived fluorescent dye of formula (I) also contains at least one reducing agent as defined above. This composition is then applied to the hair.

When the phenylpyrido[1,2-a]indolinium-derived thiol fluorescent dye of formula (I) for which m and n are 1 comprises a thiol-function-protecting group Y, the process of the invention may be preceded by a deprotection step aimed at restoring the SH function in situ.

By way of example, it is possible to deprotect the S—Y function of the dyes of the invention with a Y protecting group by adjusting the pH as follows:

| Y: Protecting group | Deprotection |
|---|---|
| alkylcarbonyl | pH > 9 |
| arylcarbonyl | pH > 9 |
| alkoxycarbonyl | pH > 9 |
| aryloxycarbonyl | pH > 9 |
| arylalkoxycarbonyl | pH > 9 |
| (di) (alkyl)aminocarbonyl | pH > 9 |
| (alkyl)arylaminocarbonyl | pH > 9 |
| optionally substituted aryl, such as phenyl | pH > 9 |
| 5-, 6- or 7-membered monocyclic heteroaryl such as oxazolium | pH > 9 |
| 8- to 11-membered bicyclic heteroaryl, such as benzoimidazolium or benzoxazolium | pH > 9 |

The deprotection step can also be carried out during a hair pretreatment step, for instance reducing pretreatment of the hair.

According to one variant, the reducing agent is added to the dye composition containing at least one phenylpyrido[1,2-a]indolinium-derived fluorescent dye of formula (I) at the time of use.

According to another process, the composition comprising at least one phenylpyrido[1,2-a]indolinium-derived fluorescent dye of formula (I) also contains at least one reducing agent as defined above. This composition is then applied to the hair.

According to another variant, the reducing agent is applied as a post-treatment, after the application of the composition containing at least one phenylpyrido[1,2-a]indolinium-derived fluorescent dye of formula (I). The duration of the post-treatment with the reducing agent may be short, for example from 0.1 second to 30 minutes, preferably from 1 minute to 15 minutes, with a reducing agent as described above. According to a specific embodiment, the reducing agent is an agent of thiol or borohydride type as described above.

A specific embodiment of the invention relates to a process in which the phenylpyrido[1,2-a]indolinium-derived fluorescent dye of formula (I) can be applied directly to the hair without reducing agents, free of reducing pretreatment or reducing post-treatment.

A treatment with an oxidizing agent may optionally be combined. In an embodiment of the invention the process of the invention comprises an additional step consisting in applying an oxidizing agent to the keratin fibers. Any type of oxidizing agent conventional in the field may be used. Thus, it may be chosen from hydrogen peroxide, urea peroxide, alkali metal bromates, persalts such as perborates and persulfates, and also enzymes, among which mention may be made of peroxidases, 2-electron oxidoreductases such as uricases and 4-electron oxygenases such as laccases. The use of hydrogen peroxide is particularly preferred.

The duration of the possible post-treatment with an oxidizing agent is between 1 second and 10 minutes.

The application of the dye composition according to the invention is generally carried out at ambient temperature. It may, however, be carried out at temperatures ranging from 20 to 180° C.

A subject of the invention is also a multicompartment dyeing device or dyeing "kit" in which a first compartment contains a dye composition comprising at least one phenylpyrido[1,2-a]indolinium-derived fluorescent dye of formula (I) and a second compartment contains a reducing agent capable of reducing the disulfide functions of keratin materials and/or of the phenylpyrido[1,2-a]indolinium-derived disulfide fluorescent dye of formula (I).

One of these compartments may also contain one or more other dyes of direct dye or oxidation dye type.

The invention also relates to a multicompartment device in which a first compartment contains a dye composition comprising at least one phenylpyrido[1,2-a]indolinium-derived fluorescent dye of formula (I); a second compartment contains a reducing agent capable of reducing the disulfide bond of the keratin materials and/or of the phenylpyrido[1,2-a]indolinium-derived disulfide fluorescent dye of formula (I); and a third compartment contains an oxidizing agent.

Alternatively, the dyeing device contains a first compartment containing a dye composition which comprises at least one phenylpyrido[1,2-a]indolinium-derived protected thiol fluorescent dye of formula (I) with m and n being 1, a second compartment containing an agent capable of deprotecting the protected thiol so as to free the thiol, and optionally a third compartment comprising an oxidizing agent.

Each of the devices mentioned above may be equipped with a means for delivering the desired mixture to the hair, for example such as the devices described in patent FR 2 586 913.

The examples which follow serve to illustrate the invention without, however, being limiting in nature. The dyes of the examples hereinafter have been entirely characterized by conventional spectroscopic and spectrometric methods.

EXAMPLES

Example 1

Synthesis of 2,2'-[disulfanediylbis(ethane-2,1-diyl-carbamoyl)]bis[10,10-dimethyl-8-(1-methyl-1H-indol-3-yl)-10H-pyrido[1,2-a]indolium]dichloride

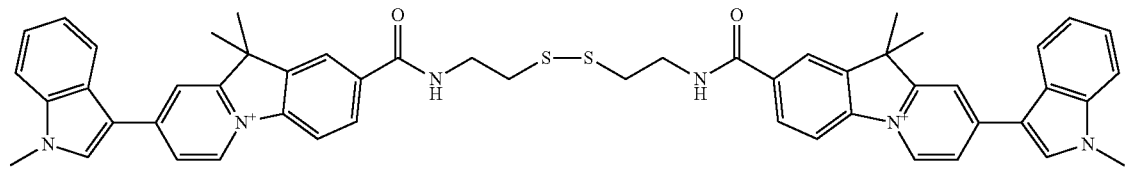

2 Cl⁻

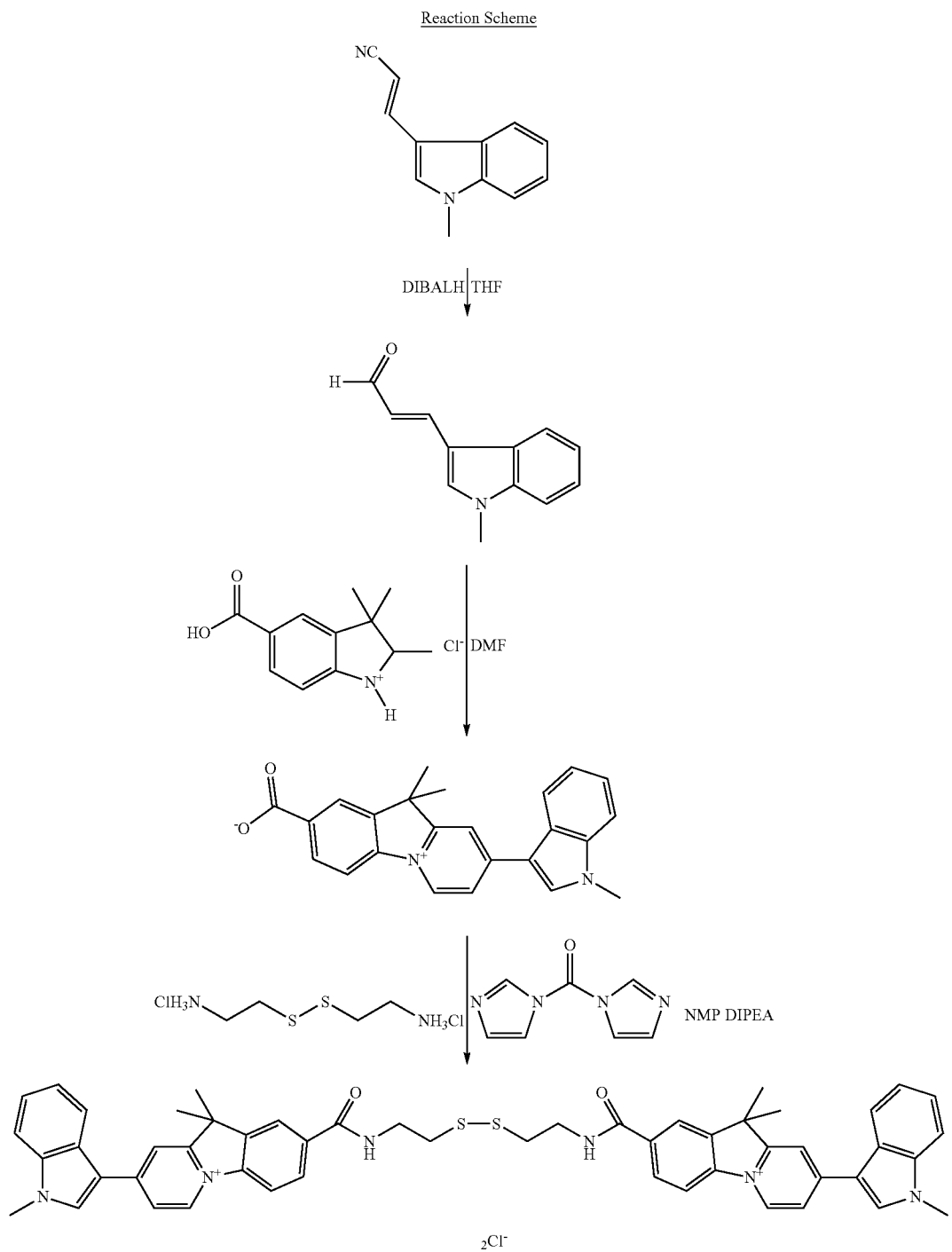

Reaction Scheme

Step 1: Synthesis 3-(1-methyl-1H-indol-3-yl)prop-2-enal

To a solution of 3-(1-methyl-1H-indol-3-yl)prop-2-enenitrile (2.883 g, 15.8 mmol) in dry THF at 0° C. was added 19 ml (19 mmol) of 1N DIBALH in cyclohexane under an argon atmosphere. The mixture was warmed to room temperature and allowed to stir for 6 h. The reaction was carefully quenched with saturated potassium sodium tartrate tetrahydrate and then extracted with ethyl acetate three times. The combined organic extracts were evaporated to dryness. The resulting residue was subjected to silica gel chromatography (eluent: hexane/ethyl acetate=4/1 to 1/1) to afford 2.37 g of compound. Analyses were in accordance with the expected structure Step 2: Synthesis of 10,10-dimethyl-8-(1-methyl-1H-indol-3-yl)-10H-pyrido[1,2-a]indolium-2-carboxylate A mixture of 3-(1-methyl-1H-indol-3-yl)prop-2-enal (2.37 g, 12.8 mmol) and 5-carboxy-2,3,3-trimethyl-3H-indolium chloride (3.06 g, 12.8 mmol) in 20 ml of DMF was heated at 120° C. for 17 h. After cooling, ether was added and the solids precipitated. The resulting solids was collected and further purified by silica gel chromatography (eluent: dichloromethane/methanol=10/1 to 2/1) to afford 0.83 g of a yellow powder.

Analyses were in accordance with the expected structure
Step 3: Synthesis of 2,2'-[disulfanediylbis(ethane-2,1-diyl-carbamoyl)]bis[10,10-dimethyl-8-(1-methyl-1H-indol-3-yl)-10H-pyrido[1,2-a]indolium]dichloride 10,10-dimethyl-8-(1-methyl-1H-indol-3-yl)-10H-pyrido-[1,2-a]indolium-2-carboxylate 0.37 g was solubilized in 5 mL N-methylpyrrolidinone (NMP), a solution of HCl in dry dioxane and diethyl ether (1 mL; 1N; 1:3) was added and 1,1'-carbonyldiimidazole (320 mg) was progressively added. After 3 h, 200 mg of cystamine dihyrochloride in mL diisopropylethylamine (DIPEA) were added to the mixture. After 24 h, the reaction mixture was poured in 100 mL acetone. The resulting solid was filtered, washed with acetone and dried under vacuum (340 mg, yellow powder). Analyses were in accordance with the expected structure.

LCMS m/z=427.5 (dication) $\lambda_{max}$: 424 nm.

Example 2

Synthesis of 2,2'-[disulfanediyl-bis(ethane-2,1-diyl-carbamoyl)]bis{8-[4-(dimethylamino)-phenyl]-10,10-dimethyl-10H-pyrido[1,2-a]indolium}-dichloride Step 1: Synthesis of 8-[4-(dimethylamino)phenyl]-10,10-dimethyl-10H-pyrido[1,2-a]indolium-2-carboxylate A suspension of 5-carboxy-2,3,3-trimethyl-3H-indolium chloride (14.5 g, 60.5 mmol) and 4-dimethylamino cinnamaldehyde (10.6 g, 60.5 mmol) in 200 ml of acetonitrile was heated to 60° C. for 24 h. The solvent was removed under vacuum and the resulting residue was subjected to silica gel chromatography twice. Then, recrystallization from methanol and ether afforded 10 g of target compound.

Analyses were in accordance with the expected structure.
Step 2: Synthesis of 2,2'-[disulfanediylbis(ethane-2,1-diyl-carbamoyl)]bis[10,10-dimethyl-8-(1-methyl-1H-indol-3-yl)-10H-pyrido[1,2-a]indolium]dichloride 8-[4-(dimethylamino)phenyl]-10,10-dimethyl-10H-pyrido-[1,2-a]indolium-2-carboxylate 1 g was solubilized in 15 mL N-methylpyrrolidinone (NMP), a solution of HCl in dry diethyl ether (3 mL; 1N) was added and 1,1'-carbonyldiimidazole (1 g) was progressively added. After 3 h, 285 mg of cystamine dihyrochloride in 1 g diisopropylethylamine (DIPEA) were added to the mixture. After 24 h, the reaction mixture was poured in 100 mL acetone. The resulting solid was filtered, washed with acetone and dried under vacuum (912 mg, pale yellow powder). Analyses were in accordance with the expected structure.

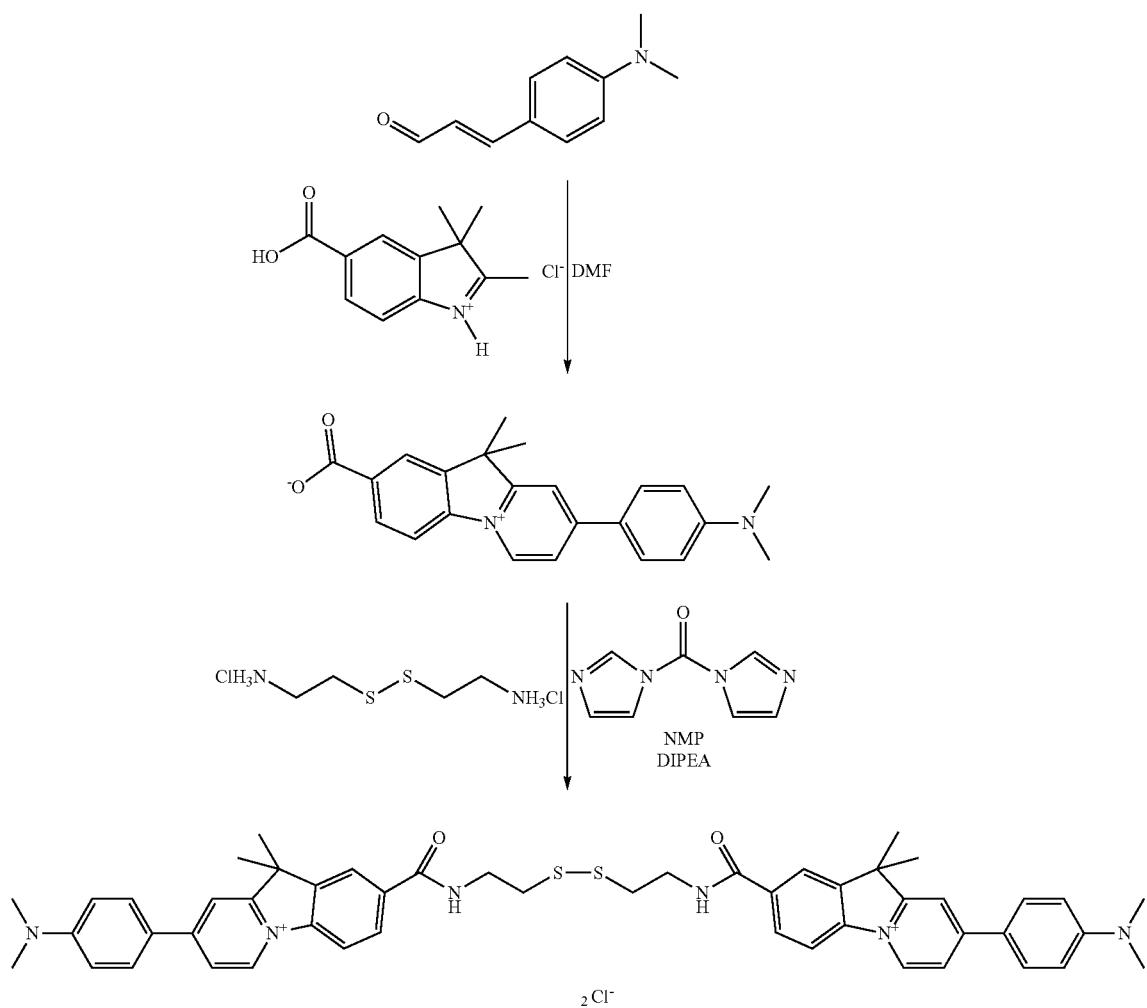

LCMS m/z=417.5 (dication) $\lambda_{max}$: 470 nm.

Dyeing Process—Compounds [1] and [2]

Preparation of a Composition A

| | |
|---|---|
| Disulfide dye of [1] or [2] | $5 \times 10^{-4}$ mol % |
| Benzyl alcohol | 4 g |
| Polyethylene glycol 6 EO | 6 g |
| Hydroxyethylcellulose | 0.7 g |
| Alkylpolyglucoside in an aqueous solution containing 65% AM | 4.5 g |
| Demineralized water | qs 100 g |

Disulfide dye [1]

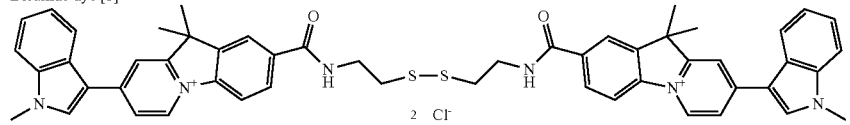

Disulfide dye [2]

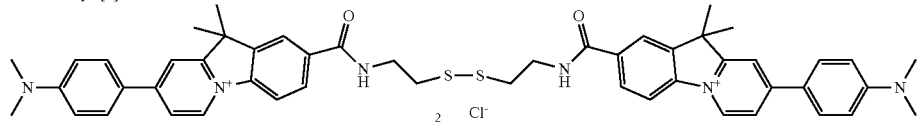

Preparation of a Composition B

| | |
|---|---|
| Thioglycolic acid | 1M |
| Sodium hydroxide | qs pH 8.5 |
| Demineralized water | qs 100 g |

At the time of use, compositions A (9 ml) and B (1 ml) are mixed, then the formulations are applied to locks of natural white hair containing 90% white hairs (NW), permanent-waved white hair (PW) or chestnut-brown hair having a tone height of 4 (TH4). The leave-in time is 20 minutes at ambient temperature (AT).

After rinsing with running water, a fixer (Dulcia Vital II®) diluted 10-fold with water is applied for 5 minutes at AT. After rinsing with running water and shampooing, the locks are air-dried. During the shampooing operations, there is no visible bleeding of the color; the shampoo foam and the rinsing water are uncolored.

(i) Dyeing

Lightening of TH4 Keratin Fibers.

A lightening of the hair thus treated with dyes 1 or 2 is observed: the locks of tone height 4 became visibly lighter than untreated control locks.

Dyeing of NW and PW Keratin Fibers:

The natural white hair and the permanent-waved white hair are colored bright orange.

Reflectance Results:

The lightening effectiveness of the compositions in accordance with the invention was expressed as a function of the reflectance of the hair. These reflectances are compared with the reflectance of a lock of untreated hair of tone height TH4 (reference) and plotted in FIG. 1. Example 3 on the spectrum corresponds to Example 1 synthesized.

The reflectance is measured by means of a KONIKA-MINOLTA®, CM 3600d spectrophotocolorimeter apparatus and after irradiation of the hair with visible light in the wavelength range of from 400 to 700 nanometers.

It is first of all noted that the reflectance of a lock of hair treated with a composition according to the invention is greater than that of untreated hair (reference). Most particularly, the reflectance of the locks treated with dye [1] (example 3 on the spectrum) and with dye [2] (example 2 on the spectrum) is much greater than that of the reference lock in the wavelength range above 460 nm on ward. The locks treated with these two compounds therefore appear to be lighter.

ii) Fastness with Respect to Successive Shampooing Operations:

The locks treated are divided into two, half are subjected to 5 successive shampooing operations according to a cycle which comprises wetting the locks with water, washing with a conventional shampoo, rinsing with water, followed by drying.

During the shampooing operations, there is no visible bleeding of the color; the shampoo foam and the rinsing water are not colored.

The color observed and the lightening effect remain visible on the hair of tone height 4 thus treated.

iii) Fastness with Respect to Light:

A study of light-fastness was carried out, by exposure to the Xenotest, on the locks of natural white NW and permanent-waved white PW hair treated with the dyeing process for 3 hours. The exposure conditions are 90 W/m², 60% relative humidity and with a chamber temperature of 35° C.

After 3 hours of exposure to the light, the colored natural white hair and the colored permanent-waved white hair dyed with dyes 1 and 2 of the invention are virtually unchanged.

The dyes of the invention are more particularly photostable.

The invention claimed is:

1. A fluorescent dye chosen from dyes of formula (I):

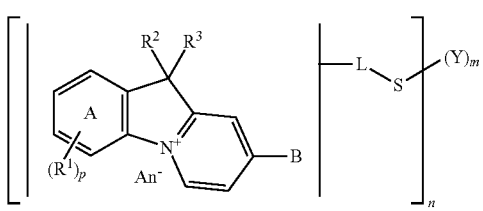

organic acid salts, mineral acid salts, optical isomers, geometric isomers, and solvates thereof,
wherein, in formula (I):
- m is 0 or 1;
- n is 1 or 2;
- p is chosen from integers ranging from 0 to 4 inclusive;
- $R^1$, which may be identical or different, are each chosen from halogens, optionally substituted ($C_1$-$C_6$)alkyl groups, ($C_1$-$C_6$)alkoxy groups, ($C_1$-$C_6$) alkylthio groups, (di)($C_1$-$C_6$) (alkyl)amino groups, ($C_1$-$C_6$)polyhaloalkyl groups, hydroxyl groups, ($C_1$-$C_6$) polyhydroxyalkyl groups, polyhydroxy ($C_1$-$C_6$)alkoxy groups, nitro groups, cyano groups, R-G-C(G')— groups, R—C(G')-G- groups, R'S($O)_2$—N(R)— groups, and RR'N—S($O)_2$— groups,
  - with G and G', independently of one another, each chosen from oxygen, sulfur, and groups NR', and
  - R and R', independently of one another, each chosen from hydrogen and ($C_1$-$C_6$) alkyl groups;
- $R^2$ and $R^3$, independently of one another, are each chosen from optionally substituted ($C_1$-$C_6$)alkyl groups;
- B is chosen from optionally substituted aryl groups and optionally substituted heteroaryl groups;
- L is chosen from divalent $C_1$-$C_{20}$ hydrocarbon-based chains which are optionally substituted, optionally interrupted, and/or optionally terminated at one end with at least one group chosen from:
  - i) divalent groups chosen from: —N($R_a$)—; —$N^+$($R_a$)($R_b$)-$An^-$; —O—; —S—; —CO—, and —$SO_2$—,
    - with $R_a$ and $R_b$, independently of one another, each chosen from hydrogen, ($C_1$-$C_6$)alkyl groups, hydroxyl ($C_1$-$C_6$)alkyl groups, and (di)($C_1$-$C_6$) (alkyl)amino ($C_1$-$C_6$)alkyl groups, and
    - $An^-$ chosen from anionic counterions, and
  - ii) cationic heterocyclic and heteroaryl $Het^+An^-$ groups, with $An^-$ chosen from anionic counterions, and
    - $Het^+$ chosen from saturated and unsaturated heterocycles comprising 5 to 10 members and saturated and unsaturated heteroaryls comprising 5 to 10 members;
- Y is chosen from:
  - i) hydrogen;
  - ii) alkali metals;
  - iii) alkaline earth metals;
  - iv) $NR^+R^\alpha R^\beta R^\gamma R^\delta An''^-$ ammonium groups and $P^+R^\alpha R^\beta R^\gamma R^\delta An''^-$ phosphonium groups,
    - with $R^\alpha$, $R^\beta$, $R^\gamma$, and $R^\delta$, independently of one another, each chosen from hydrogen and ($C_1$-$C_4$) alkyl groups, and
    - $An''^-$ chosen from anionic counterions; and
  - v) thiol-function-protecting groups;
- $An^-$ is chosen from anionic counterions;
and when n is 2, then m is zero, and when n is 1, then m is 1.

2. The fluorescent dye of formula (I) according to claim 1, wherein m and n are each 1 and Y is chosen from hydrogen and alkali metals.

3. The fluorescent dye of formula (I) according to claim 1, wherein m and n are each 1 and Y is chosen from protecting groups.

4. The fluorescent dye of formula (I) according to claim 3, wherein Y is chosen from the following protecting groups:
- ($C_1$-$C_4$)alkylcarbonyl groups;
- ($C_1$-$C_4$)alkylthiocarbonyl groups;
- ($C_1$-$C_4$)alkoxycarbonyl groups;
- ($C_1$-$C_4$)alkoxythiocarbonyl groups;
- alkylthiothiocarbonyl groups;
- (di)($C_1$-$C_4$) (alkyl)aminocarbonyl groups;
- (di)($C_1$-$C_4$) (alkyl)aminothiocarbonyl groups;
- arylcarbonyl groups;
- aryloxycarbonyl groups;
- aryl ($C_1$-$C_4$)alkoxycarbonyl groups;
- (di)($C_1$-$C_4$) (alkyl)aminocarbonyl groups;
- ($C_1$-$C_4$) (alkyl)arylaminocarbonyl groups;
- carboxyl groups;
- $SO_3^-M^+$ groups with $M^+$ chosen from alkali metals or $An^-$ and $An'^-$ groups of formula (I);
- optionally substituted aryl groups;
- optionally substituted heteroaryl groups;
- optionally cationic, optionally heterocycloalkyl groups;
- isothiouronium groups;
- —$C(NR'^cR'^d)=N^+R'^eR'^fAn''''^-$, with $R'^c$, $R'^d$, $R'^e$ and $R'^f$, independently of one another, each chosen from hydrogen and ($C_1$-$C_4$)alkyl groups, and $An''''^-$ chosen from anionic counterions;
- isothiourea groups;
- —$C(NR'^cR'^d)=NR'^e$, with $R'^c$, $R'^d$, and $R'^e$, independently of one another, each chosen from hydrogen and ($C_1$-$C_4$) alkyl groups;
- optionally substituted (di)aryl ($C_1$-$C_4$)alkyl groups;
- optionally substituted (di)heteroaryl ($C_1$-$C_4$)alkyl groups;
- —$CR^1R^2R^3$, with $R^1$, $R^2$, and $R^3$, independently of one another, each chosen from
  - halogens;
  - optionally substituted aryl groups;
  - optionally substituted heteroaryl groups; and
  - $P(Z^1)R'^1R'^2R'^3$, with $R'^1$ and $R'^2$, independently of one another, each chosen from hydroxyl groups, ($C_1$-$C_4$) alkoxy groups, alkyl groups, $R'^3$ chosen from hydroxyl groups and ($C_1$-$C_4$)alkoxy groups, and $Z^1$ chosen from oxygen and sulfur;
- sterically hindered cyclic groups;
- optionally substituted alkoxyalkyl groups; and
- groups of the following formula:

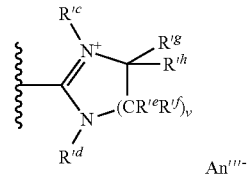

with
- $R'^c$, $R'^d$, $R'^e$, $R'^f$, $R'^g$, and $R'^h$, independently of one another, each chosen from hydrogen and ($C_1$-$C_4$)alkyl groups,
- or two groups $R'^g$ with $R'^h$ and/or $R'^e$ with $R'^f$ form an oxo or thioxo group or $R'^g$ with $R'^e$ together form a cycloalkyl group; and v is chosen from integers ranging from 1 to 3 inclusive; and An'''− is chosen from anionic counterions.

5. The fluorescent dye according to claim 4, wherein R'$^c$, R'$^d$, R'$^e$, R'$^f$, R'$^g$, and R'$^h$ are hydrogen.

6. The fluorescent dye according to claim 1, wherein Y is chosen from alkali metals and protecting groups chosen from:
- ($C_1$-$C_4$)alkylcarbonyl groups;
- arylcarbonyl groups;
- ($C_1$-$C_4$)alkoxycarbonyl groups;
- aryloxycarbonyl groups;
- aryl ($C_1$-$C_4$)alkoxycarbonyl groups;
- (di)($C_1$-$C_4$) (alkyl)aminocarbonyl groups;
- ($C_1$-$C_4$) (alkyl) arylaminocarbonyl groups;
- optionally substituted aryl groups;
- 5- and 6-membered cationic monocyclic heteroaryl groups optionally substituted with at least one ($C_1$-$C_4$)alkyl group which may be identical or different;
- 8- to 11-membered cationic bicyclic heteroaryl groups optionally substituted with at least one ($C_1$-$C_4$)alkyl group which may be identical or different;
- cationic heterocyclic groups of the following formula:

[structure of imidazolinium with Me groups and An''' counterion]

- isothiouronium —C($NH_2$)=$N^+H_2$An'''$^-$ groups, with An'''$^-$ chosen from anionic counterions;
- isothiourea —C($NH_2$)=NH groups; and
- $SO_3^-M^+$ with M+ chosen from alkali metals or An$^-$ and An'$^-$ groups of formula (I).

7. The fluorescent dye according to claim 1, wherein n is 2 and m is 0.

8. The fluorescent dye according to claim 1, having formula (Ia):

[structure of formula (Ia)]

wherein, in formula (Ia):
X is chosen from -G-, -G'-C(G)- and —C(G)-G'-, with G and G', independently of one another, chosen from oxygen, sulfur, NR groups with R chosen from hydrogen and ($C_1$-$C_6$)alkyl groups; X being linked to the rest of the molecule by A or B;

L' is chosen from
- saturated, hydrocarbon-based $C_2$-$C_9$ alkylene groups optionally interrupted with a group chosen from —N(R'$_a$)- groups; —$N^+$(R'$_a$)(R'$_b$)-An$^-$ groups; —C(O)—N(R'$_a$)— groups; and —N(R'$_a$)—C(O)— groups; and
- divalent cationic heteroaryl groups comprising 5 to 7 members, with R'$_a$ and R'$_b$, independently of one another, each chosen from hydrogen and ($C_1$-$C_6$) alkyl groups, and An$^-$ chosen from anionic counterions; and $R^2$ and $R^3$, independently of one another, are each chosen from $C_1$-$C_3$ alkyl groups.

9. The fluorescent dye according to claim 1, wherein, the fluorescent dye is chosen from the following dyes:

1

[chemical structure 1]

2

[chemical structure 2]

-continued
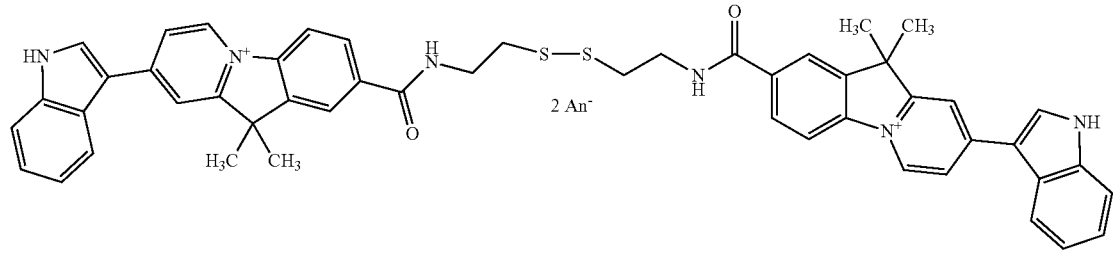
3
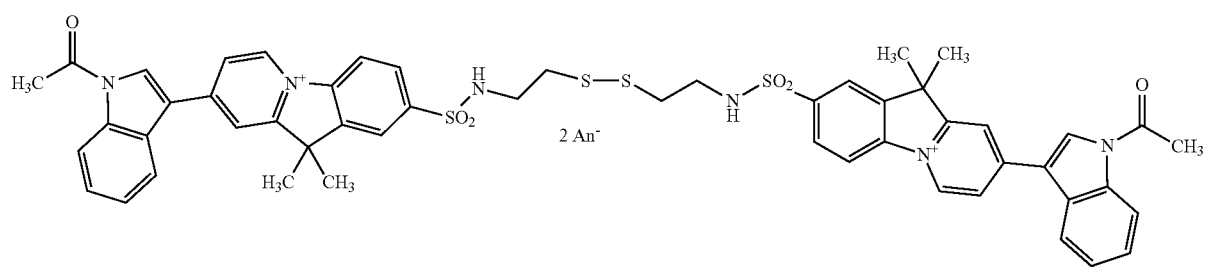
4
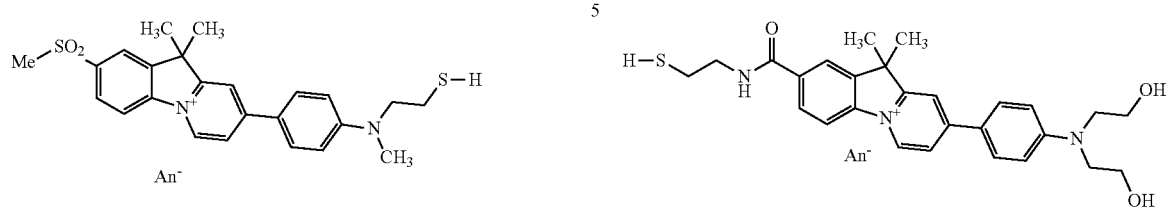
5 6
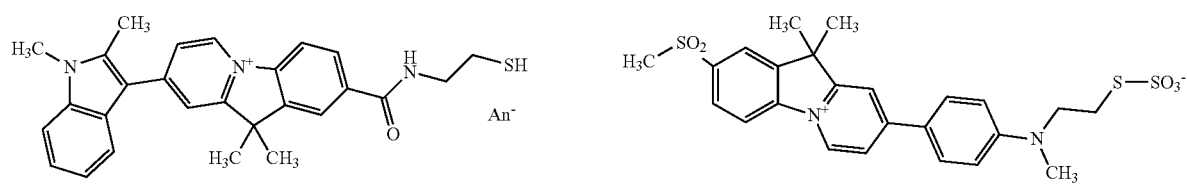
7 8
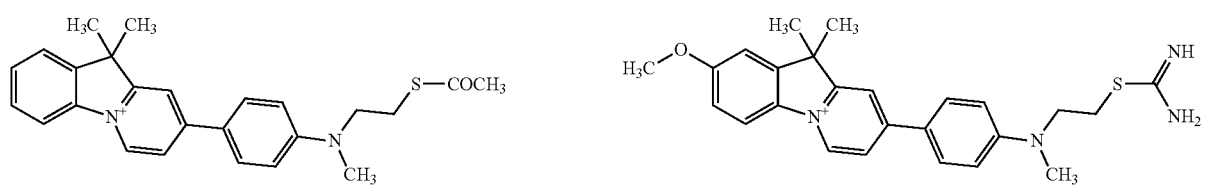
9 10
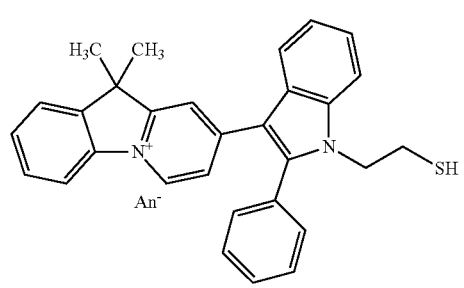
11

-continued
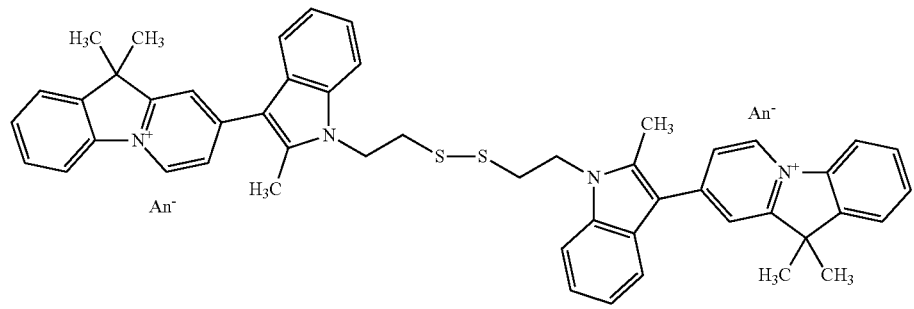
12
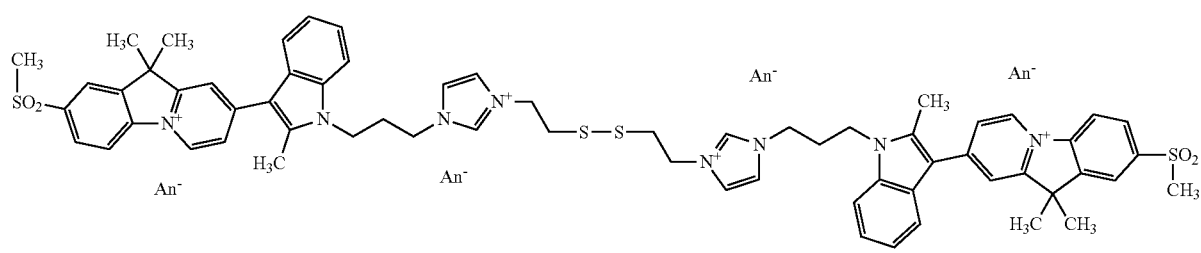
13
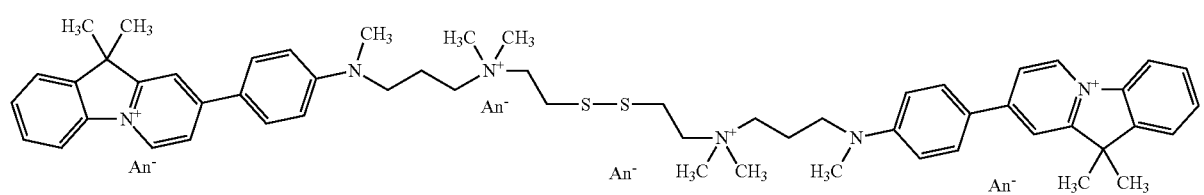
14
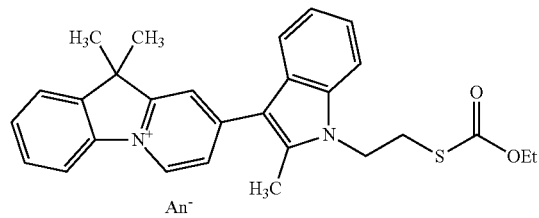
15
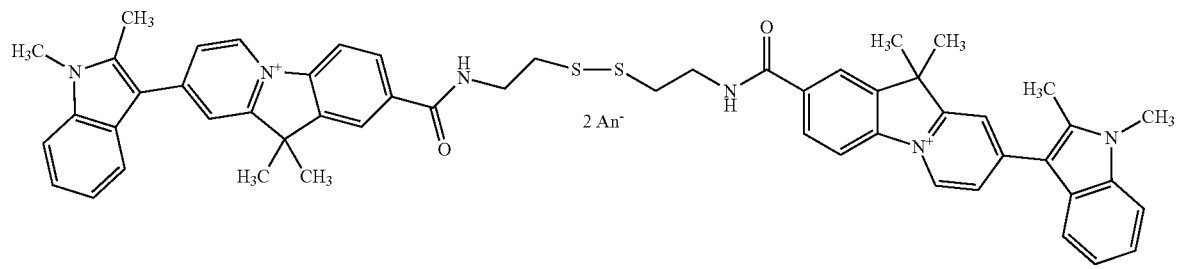
16
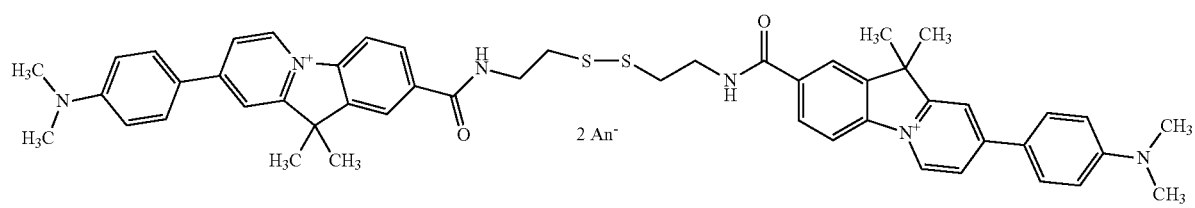
17

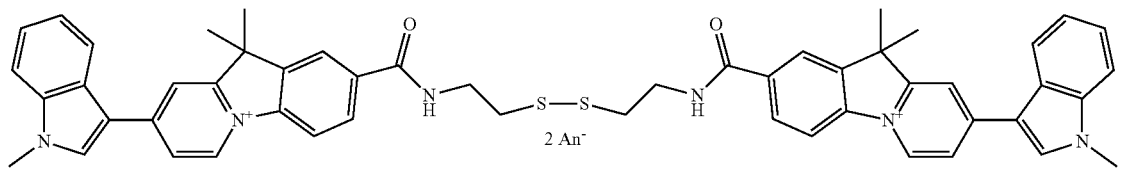

with An⁻, which may be identical or different, chosen from anionic counterions.

10. A dye composition comprising a suitable cosmetic medium and at least one fluorescent dye according to claim 1.

11. A dye composition according to claim 10, wherein the dye composition further comprises at least one reducing agent.

12. A process for dyeing keratin materials, in which a suitable dye composition comprising at least one fluorescent dye chosen from dyes of formula (I):

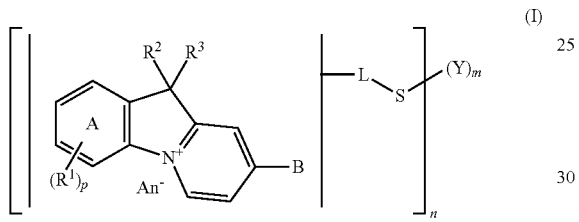

organic acid salts, mineral acid salts, optical isomers, geometric isomers, and solvates thereof,
wherein, in formula (I):
m is 0 or 1;
n is 1 or 2;
p is chosen from integers ranging from 0 to 4 inclusive;
R₁, which may be identical or different, are each chosen from halogens, optionally substituted (C₁-C₆)alkyl groups, (C₁-C₆)alkoxy groups, (C₁-C₆) alkylthio groups, (di)(C₁-C₆) (alkyl)amino groups, (C₁-C₆)polyhaloalkyl groups, hydroxyl groups, (C₁-C₆) polyhydroxyalkyl groups, polyhydroxy (C₁-C₆)alkoxy groups, nitro groups, cyano groups, R-G-C(G')- groups, R—C(G')-G- groups, R'S(O)₂—N(R)— groups, and RR'N—S(O)₂— groups,
  with G and G', independently of one another, each chosen from oxygen, sulfur, and groups NR', and
  R and R', independently of one another, each chosen from hydrogen and (C₁-C₆) alkyl groups;
R² and R³, independently of one another, are each chosen from optionally substituted (C₁-C₆)alkyl groups;
B is chosen from optionally substituted aryl groups and optionally substituted heteroaryl groups;
L is chosen from divalent C₁-C₂₀ hydrocarbon-based chains which are optionally substituted, optionally interrupted, and/or optionally terminated at one end with at least one group chosen from:
  i) divalent groups chosen from: —N(Rₐ)—; —N⁺(Rₐ)(Rᵦ)—An⁻; —O—; —S—; —CO—, and —SO₂—,
    with Rₐ and Rᵦ, independently of one another, each chosen from hydrogen, (C₁-C₆)alkyl groups, hydroxyl (C₁-C₆)alkyl groups, and (di)(C₁-C₆)(alkyl)amino (C₁-C₆)alkyl groups, and
    An⁻ chosen from anionic counterions, and
  ii) cationic heterocyclic and heteroaryl Het⁺An''⁻ groups, with An⁻ chosen from anionic counterions, and
    Het⁺ chosen from saturated and unsaturated heterocycles comprising 5 to 10 members and saturated and unsaturated heteroaryls comprising 5 to 10 members;
Y is chosen from:
  i) hydrogen;
  ii) alkali metals;
  iii) alkaline earth metals;
  iv) N⁺RᵅRᵝRᵞRᵟAn'''⁻ ammonium groups and P⁺RᵅRᵝRᵞRᵟAn'''⁻ phosphonium groups,
    with Rᵅ, Rᵝ, Rᵞ, and Rᵟ, independently of one another, each chosen from hydrogen and (C₁-C₄) alkyl groups, and
    An'''⁻ chosen from anionic counterions; and
  v) thiol-function-protecting groups; and
An⁻ is chosen from anionic counterions;
  and when n is 2, then m is zero, and when n is 1, then m is 1, is applied to the materials.

13. The process for dyeing keratin materials according to claim 12, wherein the keratin materials are dark keratin fibers having a tone height of less than or equal to 6.

14. A multicompartment device in which a first compartment contains a dye composition comprising at least one fluorescent dye of chosen from dyes of formula (I):

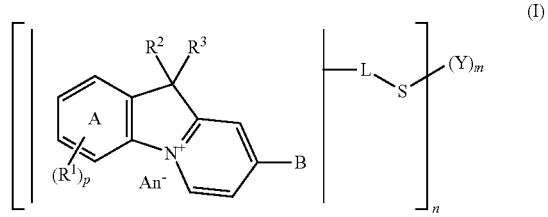

organic acid salts, mineral acid salts, optical isomers, geometric isomers, and solvates thereof,
wherein, in formula (I):
m is 0 or 1;
n is 1 or 2;
p is chosen from integers ranging from 0 to 4 inclusive;
R¹, which may be identical or different, are each chosen from halogens, optionally substituted (C₁-C₆)alkyl groups, (C₁-C₆)alkoxy groups, (C₁-C₆)alkylthio groups, (di)(C₁-C₆) (alkyl)amino groups, (C₁-C₆)polyhaloalkyl groups, hydroxyl groups, (C₁-C₆) polyhydroxyalkyl groups, polyhydroxy (C₁-C₆)alkoxy groups, nitro groups, cyano groups, R-G-C(G')- groups, R—C(G')-G- groups, R'S(O)₂—N(R)— groups, and RR'N—S(O)₂— groups, with G and G', independently of one another, each chosen from oxygen, sulfur, and groups NR', and R and R', independently of one another, each chosen from hydrogen and $(C_1-C_6)$ alkyl groups;

$R^2$ and $R^3$, independently of one another, are each chosen from optionally substituted $(C_1-C_6)$alkyl groups;

B is chosen from optionally substituted aryl groups and optionally substituted heteroaryl groups;

L is chosen from divalent $C_1-C_{20}$ hydrocarbon-based chains which are optionally substituted, optionally interrupted, and/or optionally terminated at one end with at least one group chosen from:
  i) divalent groups chosen from: —$N(R_a)$—; —$N^+(R_a)(R_b)$—$An^-$; —O—; —S—; —CO—, and —$SO_2$—, with $R_a$ and $R_b$, independently of one another, each chosen from hydrogen, $(C_1-C_6)$alkyl groups, hydroxyl $(C_1-C_6)$alkyl groups, and (di)$(C_1-C_6)$(alkyl)amino $(C_1-C_6)$alkyl groups, and $An^-$ chosen from anionic counterions, and
  ii) cationic heterocyclic and heteroaryl $Het^+An^-$ groups, with $An^-$ chosen from anionic counterions, and $Het^+$ chosen from saturated and unsaturated heterocycles comprising 5 to 10 members and saturated and unsaturated heteroaryls comprising 5 to 10 members;

Y is chosen from:
  i) hydrogen;
  ii) alkali metals;
  iii) alkaline earth metals;
  iv) $NR^+R^\alpha R^\beta R^\gamma R^\delta An''^-$ ammonium groups and $P^+R^\alpha R^\beta R^\gamma R^\delta An''^-$ phosphonium groups, with $R^\alpha$, $R^\beta$, $R^\gamma$, and $R^\delta$, independently of one another, each chosen from hydrogen and $(C_1-C_4)$ alkyl groups, and $An''^-$ chosen from anionic counterions; and
  v) thiol-function-protecting groups; and $An^-$ is chosen from anionic counterions;

and when n is 2, then m is zero, and when n is 1, then m is 1.

\* \* \* \* \*